United States Patent
Iwakiri et al.

(10) Patent No.: US 9,322,928 B2
(45) Date of Patent: Apr. 26, 2016

(54) RADIATION IMAGING APPARATUS, METHOD FOR CONTROLLING THE SAME, AND RADIATION IMAGE DETECTION DEVICE

(71) Applicant: FUJIFILM Corporation, Tokyo (JP)

(72) Inventors: Naoto Iwakiri, Ashigarakami-gun (JP); Naoyuki Nishino, Ashigarakami-gun (JP); Yasunori Ohta, Ashigarakami-gun (JP); Kouichi Kitano, Ashigarakami-gun (JP); Haruyasu Nakatsugawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 266 days.

(21) Appl. No.: 14/139,306

(22) Filed: Dec. 23, 2013

(65) Prior Publication Data
US 2014/0110595 A1 Apr. 24, 2014

Related U.S. Application Data

(63) Continuation of application No. PCT/JP2012/068940, filed on Jul. 26, 2012.

(30) Foreign Application Priority Data

Jul. 26, 2011 (JP) .................. 2011-163478

(51) Int. Cl.
*A61B 6/00* (2006.01)
*G01T 1/16* (2006.01)
*H04N 5/32* (2006.01)
*H04N 5/353* (2011.01)
*H04N 5/374* (2011.01)

(52) U.S. Cl.
CPC .................. *G01T 1/16* (2013.01); *A61B 6/4233* (2013.01); *A61B 6/4283* (2013.01); *H04N 5/32* (2013.01); *A61B 6/54* (2013.01); *H04N 5/353* (2013.01); *H04N 5/374* (2013.01)

(58) Field of Classification Search
CPC ........ A61B 6/54; A61B 6/542; A61B 6/4233; A61B 6/4283; H04N 5/32; H04N 5/353; H04N 5/374; G01T 1/16
See application file for complete search history.

(56) References Cited

U.S. PATENT DOCUMENTS

| | | | |
|---|---|---|---|
| 6,454,460 B1 * | 9/2002 | Ramanathan | A61B 6/583 378/158 |
| 2003/0142784 A1 * | 7/2003 | Suzuki | G01N 23/04 378/58 |
| 2006/0071171 A1 * | 4/2006 | Kameshima | A61B 6/00 250/370.09 |

FOREIGN PATENT DOCUMENTS

JP 2002-301053 A 10/2002
JP 2006-122667 A 5/2006

OTHER PUBLICATIONS

International Search Report, issued in PCT/JP2012/068940, dated Sep. 11, 2012.
Written Opinion of the International Search Authority, issued in PCT/JP2012/068940, dated Sep. 11, 2012.
Forms PCT/IB/338, PCT/IB/373 and PCT/ISA/237 dated Feb. 6, 2014 for International Application No. PCT/JP2012/068940.

* cited by examiner

*Primary Examiner* — Glen Kao
(74) *Attorney, Agent, or Firm* — Birch, Stewart, Kolasch & Birch, LLP

(57) ABSTRACT

A determination section of an FPD checks external information against a determination table and determines whether detection of a rise of X-ray pulses is allowed based on an output voltage from a short-circuited pixel. The FPD detects X-ray images. The external information is transmitted from an imaging control device. The X-ray pulses are sequentially generated by an X-ray generating apparatus. A controller selects a pulse irradiation mode in a case where the detection of the rise of the X-ray pulse is allowed. If not, a successive irradiation mode is selected. In the pulse irradiation mode, the rise and the fall of the X-ray pulse are detected and timing of storage operation is synchronized with the detected timing of the rise. In the successive irradiation mode, the storage operation is performed at predetermined time intervals without the detection of the rise and the fall of the X-ray pulse.

19 Claims, 13 Drawing Sheets

FIG. 4

| DETERMINATION TABLE FOR X-RAY TUBE α (DIODE) 65 | | | | | | | |
|---|---|---|---|---|---|---|---|
| | | TUBE CURRENT (mA) | | | | | |
| | | $I_1$ | $I_2$ | $I_3$ | $I_4$ | | $I_n$ |
| FRAME RATE (fps) | $F_1$ | B | A | A | A | | A |
| | $F_2$ | B | B | A | A | | A |
| | $F_3$ | B | B | B | A | | A |
| | $F_4$ | B | B | B | B | | A |
| | $F_n$ | B | B | B | B | | B |

FIG. 5

| DETERMINATION TABLE FOR X-RAY TUBE $\beta$ (TRIODE) 68 | | | | | | | |
|---|---|---|---|---|---|---|---|
| | | TUBE CURRENT (mA) | | | | | |
| | | $I_1$ | $I_2$ | $I_3$ | $I_4$ | | $I_n$ |
| FRAME RATE (fps) | $F_1$ | A | A | A | A | | A |
| | $F_2$ | B | A | A | A | | A |
| | $F_3$ | B | B | A | A | | A |
| | $F_4$ | B | B | B | A | | A |
| | | | | | | | |
| | $F_n$ | B | B | B | B | | B |

RADIATION IMAGING APPARATUS, METHOD FOR CONTROLLING THE SAME, AND RADIATION IMAGE DETECTION DEVICE

BACKGROUND OF THE INVENTION

1. Field of the Invention

The present invention relates to a radiation imaging apparatus for capturing a radiation image of an object, a method for controlling the same, and a radiation image detection device.

2. Description Related to the Prior Art

In the medical field, a radiation imaging system using radiation, for example, X-rays is known. An X-ray imaging system comprises an X-ray generating apparatus and an X-ray imaging apparatus. The X-ray generating apparatus comprises an X-ray tube for generating the X-rays. The X-ray imaging apparatus comprises an X-ray image detection device and peripheral devices such as an imaging control device and a console. The X-rays passed through an object is incident on the X-ray image detection device and thereby the X-ray image detection device detects an X-ray image representing image information of the object. The imaging control device controls the X-ray image detection device. Imaging conditions are provided to the X-ray generating apparatus. The imaging conditions include a tube current and a tube voltage. The tube current determines a radiation dose (hereinafter simply referred to as the dose) or amount of X-ray irradiation per unit time. The tube voltage determines radiation quality (energy spectrum) of the X-rays. The imaging conditions are set for each image capture, in consideration of a site (object) to be captured in an X-ray examination and age of a patient or subject, for example. The X-ray generating apparatus allows the X-ray tube to emit the X-rays in accordance with the imaging conditions.

X-ray image detection devices employing an X-ray image detector (FPD: Flat Panel Detector) instead of a conventional X-ray film or an imaging plate (IP) are in actual use (see Japanese Patent Laid-Open Publication No. 2002-301053). The FPD comprises a detection panel and a signal processing circuit. The detection panel has an image capture field in which pixels and signal lines are arranged. The pixels are arranged in matrix. Each pixel stores a signal charge in accordance with an amount of the incident X-rays. The signal line is connected to the pixels to read out the signal charges from the pixels. The signal processing circuit reads out the signal charges, stored in the pixels, as voltage signals and converts the voltage signals into digital image data. Thereby an X-ray image is viewed immediately after the image capture with the use of the X-ray image detection device employing the FPD.

In the detection panel, each pixel in the image capture field is composed of a photodiode, being a photoelectric conversion element, and a TFT (Thin Film Transistor). A scintillator (phosphor) is provided over the image capture field. The scintillator converts the X-rays into visible light. The TFT is a switching element that turns on and off the electric connection, between the photodiode and the signal line, to switch the operation of the pixel. When the TFT is turned off, the photodiode and the signal line are out of conduction. Thereby a storage operation, in which the signal charge is stored in the photodiode, is started. When the TFT is turned on, the photodiode conducts with the signal line. Thereby a readout operation, in which the signal charge is read out from the photodiode through the TFT and the signal line, is started.

The FPD differs from the X-ray film and the IP plate in that synchronous control is necessary. In the synchronous control, the start of the storage operation and the start of the readout operation are synchronized with timing of the X-ray irradiation. Examples of synchronous control methods include a method in which a synchronization signal is transmitted between the X-ray generating apparatus and the X-ray image detection device, and a method in which an X-ray image detection device measures X-ray intensity and monitors changes in the X-ray intensity to self-detect the timing of the start and the end of the X-ray irradiation.

As described in the Japanese Patent Laid-Open Publication No. 2002-301053, the X-ray image detection device allows the FPD to repeat the storage operation and the readout operation alternately at a predetermined frame rate. Thereby, moving images (fluoroscopic images) are captured using fluoroscopy or the like. During the fluoroscopy, the X-ray generating apparatus performs successive X-ray irradiation of substantially constant intensity (dose per unit time) or pulsed X-ray irradiation at a predetermined period as disclosed in Japanese Patent Laid-Open Publication No. 2006-122667.

The total dose during the fluoroscopy using the pulse irradiation is less than that using the successive irradiation because the X-rays are emitted intermittently in the pulse irradiation. The reduction in the total dose allows an increase in the intensity of the X-ray pulses in the pulse irradiation. Thus the pulse irradiation improves image quality while reducing an exposure dose of a subject. In a case where the fluoroscopy is performed using the pulse irradiation, the X-ray image detection device needs to perform synchronized control, namely, to detect timing of emission of each X-ray pulse to synchronize the timing with the storage operation of the FPD. Generally, the X-ray image detection device receives a synchronization signal from the X-ray generating apparatus to perform the synchronous control, which is called a communication method. However, it is impossible to perform the synchronous control using the communication method if the X-ray generating apparatus does not have a communication function.

The X-ray image detection device disclosed in the Japanese Patent Laid-Open Publication No. 2006-122667 is provided with a pulse detecting means. The pulse detecting means monitors changes in intensity of X-ray pulses to detect rises and falls of the X-ray pulses and thereby self-detects timing of the emissions of the X-ray pulses. The X-ray image detection device performs the synchronous control using a self detection method in which the operation of the FPD is synchronized with the emission timing detected by the pulse detecting means. The X-ray image detection device employing the synchronous control using the self detection method (hereinafter simply referred to as the synchronous control) is capable of performing the fluoroscopy using the pulse irradiation even if the X-ray image detection device cannot communicate with the X-ray generating apparatus.

However, the synchronous control has certain limits. The synchronous control cannot be performed depending on a period of an X-ray pulse, a duration of a wave tail of an X-ray pulse, or the like. FIGS. 12 and 13 show irradiation profiles each representing changes in X-ray intensity with time during the fluoroscopy using the pulse irradiation. As shown in FIG. 12, the X-ray generating apparatus starts applying a voltage when it receives a start command. When the voltage is applied, the X-ray intensity rises. The X-ray intensity reaches a peak value in accordance with a tube current and is maintained at a substantially constant value. Upon receiving a stop command, an X-ray generating apparatus stops applying the voltage and thereby the X-ray intensity falls. Thus a single X-ray pulse is generated. These steps are repeated at regular time intervals and thereby the X-ray pulses are emitted at a constant pulse period. The rise (start of the irradiation) and the fall (the end of the irradiation) of a single pulse are detected by comparing a voltage signal representing the X-ray intensity with a threshold voltage Vth. An X-ray generating apparatus with an X-ray tube composed of a commonly-used diode exhibits a relatively slow response speed to a stop command, so that time between the X-ray generating apparatus receiving the stop command and the X-ray intensity reaching "0", that is, a duration Ts of a wave tail of the X-ray pulse, becomes long.

As shown in FIG. 12, in a case where a pulse period PP (denoted as PP1 in FIG. 12) is relatively long, the wave tail of the preceding X-ray pulse does not overlap a rising edge of the subsequent X-ray pulse even if the duration of the wave tail of the preceding X-ray pulse is long. A boundary between the two successive pulses is distinct. At a valley between the two pulses, the X-ray intensity is less than the threshold voltage Vth. Hence, the rises and the falls of the X-ray pulses are surely detected using the above-described pulse detecting means.

On the other hand, as shown in FIG. 13, in a case where the pulse period PP (denoted as PP2 in FIG. 13) is relatively short, the wave tail of the preceding X-ray pulse overlaps the rising edge of the subsequent X-ray pulse if the duration of the wave tail of the preceding X-ray pulse is long. A peak of the X-ray pulse and the valley between the X-ray pulses are indistinct. In FIG. 13, each portion with hatch lines represent an overlapping portion between the two X-ray pulses and increase in X-ray intensity due to the overlap. In the irradiation profile of FIG. 13, the X-ray intensity is maintained to be greater than the threshold value Vth due to the overlap of the X-ray pulses. This state is substantially similar to successive X-ray irradiation. In this case, the detection of the rises and the falls of the X-ray pulses and the synchronous control may not be feasible, depending on the type of the pulse detecting means.

To solve the above problem, an operator may use an X-ray generating apparatus with an X-ray tube, such as a triode or tetrode, having a fast response speed and a function to immediately attenuate the wave tail of the X-ray pulse. Thereby the overlaps between the successive X-ray pulses are eliminated and the rises and the falls of the X-ray pulses are detected. Thus, the synchronous control is performed.

However, the X-ray generating apparatus comprising the X-ray tube with the fast response speed is expensive, which increases replacement cost. Even if such X-ray generating apparatus is used, the self detection may not be allowed in a case where a frame rate of the fluoroscopy is extremely short. Thus, in some cases, the synchronous control is not feasible.

Another solution to the problem is to calculate an overlapping state of two successive X-ray pulses by an operator to determine whether the synchronous control is allowed. A duration of a wave tail of an X-ray pulse varies with a tube current, a tube voltage, and a capacity obtained in a case where the X-ray tube is considered as a resistance. The tube current and the tube voltage are changed per image capture. Hence, the calculation of the duration of a wave tail of the X-ray pulse is feasible in a case where the type of the X-ray tube, the tube current, and the tube voltage are available. The calculation of the overlapping state of the two successive X-ray pulses is feasible in a case where the calculated duration of the wave tail of the X-ray pulse and a pulse period are available. The pulse period is set in accordance with a frame rate of the fluoroscopy.

However, the calculation of the overlapping state of the X-ray pulses by an operator is extremely complicated and not practical because the calculation must be done in accordance with the tube current and the tube voltage which are changed per image capture even if the same X-ray tube is used.

Even if the X-ray tube with the fast response speed is used or the operator calculated the overlapping state of the X-ray pulses, an additional measure is necessary in a case where the synchronous control is not feasible.

The Japanese Patent Laid-Open Publication Nos. 2002-301053 and 2006-122667 do not point out explicitly or suggest the above-described problems and their solutions.

SUMMARY OF THE INVENTION

An object of the present invention is to provide a radiation imaging apparatus, a method for controlling the same, and a radiation image detection device, capable of appropriate operation control in accordance with an irradiation profile of a radiation generating apparatus while cost increase and complicated operation are avoided, even if a radiation imaging apparatus is used in combination with a radiation generating apparatus incapable of communication, for performing fluoroscopy.

In order to achieve the above and other objects, the radiation imaging apparatus of the present invention comprises an image detector, a radiation detector, a controller, a determination section, and a mode setting section. The radiation imaging apparatus is used in combination with a radiation generating apparatus, for performing fluoroscopy. The radiation generating apparatus successively generates pulses of radiation to perform pulse irradiation. The image detector detects a radiation image of an object. The image detector has an image capture field in which pixels are arranged in a matrix. The each pixel stores a signal charge in accordance with a dose of the radiation. The radiation detector detects the radiation and outputs a detection signal in accordance with the dose. The controller allows the image detector to operate in one of a pulse irradiation mode and a successive irradiation mode. In the pulse irradiation mode, the controller detects a rise and a fall of the pulse of the radiation based on the detection signal outputted from the radiation detector and determines start timing of a storage operation based on timing of detecting the rise and determines start timing of a readout operation based on timing of detecting the fall. The signal charge is stored in the storage operation. The stored signal charge is read out in the readout operation. In the successive irradiation mode, the storage operation and the readout operation are repeated alternately at predetermined time intervals without detection of the rise and the fall of the pulse of the radiation. The determination section obtains external information, which includes information related to the radiation generating apparatus and imaging conditions, and determines whether the image detector is allowed to be set to the pulse irradiation mode based on the obtained external information. The mode setting section sets the image detector to one of the pulse irradiation mode and the successive irradiation mode based on a result of determination of the determination section. The mode setting section sets the image detector to the pulse irradiation mode in a case where the image detector is allowed to be set to the pulse irradiation mode. The mode setting section sets the image detector to the successive irradiation mode in a case where the image detector is not allowed to be set to the pulse irradiation mode.

It is preferable that the external information is information for determining an overlapping state of a rising edge and a falling edge of the two successive pulses of the radiation during the pulse irradiation.

It is preferable that the information related to the radiation generating apparatus is a type of a radiation tube constituting the radiation generating apparatus. It is preferable that the imaging condition is at least one of a frame rate of the fluoroscopy, a tube current supplied to the radiation tube, and a tube voltage supplied to the radiation tube.

It is preferable that the radiation imaging apparatus further comprises a determination table against which the determination section checks the external information to determine whether the pulse irradiation mode is allowed.

It is preferable that the determination table stores information of whether the pulse irradiation mode is allowed, per combination of three types of information, and the three types of information includes the type of the radiation tube, at least one of the tube current and the tube voltage, and the frame rate.

It is preferable that the determination section calculates the overlapping state based on the external information to determine whether the pulse irradiation mode is allowed.

It is preferable that the determination section sets the image detector to the successive irradiation mode in a case where the determination section cannot obtain the external information necessary for determining whether the pulse irradiation mode is allowed.

It is preferable that the radiation imaging apparatus further comprises a radiation image detection device having the image detector, the controller, and a housing for accommodating the image detector and the controller.

It is preferable that the radiation image detection device comprises the determination section.

It is preferable that the radiation image detection device has the determination table.

It is preferable that the radiation image detection device has the radiation detector.

It is preferable that the radiation imaging apparatus further comprises a peripheral device separately from the radiation image detection device, and the determination section is provided in the peripheral device.

It is preferable that the controller allows starting the storage operation at the timing of detecting the rise of the pulse of the radiation in the pulse irradiation mode.

It is preferable that the controller ends the storage operation and allows starting the readout operation at the timing of detecting the fall of the pulse of the radiation in the pulse irradiation mode.

It is preferable that the radiation imaging apparatus is capable of performing still image capture in addition to the fluoroscopy.

It is preferable that the controller detects the rise and the fall of the pulse of the radiation based on the detection signal of the radiation detector and synchronizes the storage operation with the rise and synchronizes the readout operation with the fall in the still image capture, in a manner similar to the pulse irradiation mode.

It is preferable that the image capture field includes at least one short-circuited pixel, which is constantly short-circuited with a signal line for reading out the signal charge from the pixel, in addition to the pixels. It is preferable that the short-circuited pixel, being the radiation detector, constantly outputs a signal charge corresponding to the dose to the signal line.

A radiation image detection device of the present invention comprises an image detector, a radiation detector, a controller, a determination section, and a mode setting section. The radiation image detection device is used in combination with a radiation generating apparatus, for performing fluoroscopy. The radiation generating apparatus successively generates pulses of radiation to perform pulse irradiation. The image detector detects a radiation image of an object. The image detector has an image capture field in which pixels are arranged in a matrix. The each pixel stores a signal charge in accordance with a dose of the radiation. The radiation detector detects the radiation and outputs a detection signal in accordance with the dose. The controller allows the image detector to operate in one of a pulse irradiation mode and a successive irradiation mode. In the pulse irradiation mode, the controller detects a rise and a fall of the pulse of the radiation based on the detection signal outputted from the radiation detector and determines start timing of a storage operation based on timing of detecting the rise and determines start timing of a readout operation based on timing of detecting the fall. The signal charge is stored in the storage operation. The stored signal charge is read out in the readout operation. In the successive irradiation mode, the storage operation and the readout operation are repeated alternately at predetermined time intervals without detection of the rise and the fall of the pulse of the radiation. The determination section obtains external information, which includes information related to the radiation generating apparatus and imaging conditions, and determines whether the image detector is allowed to be set to the pulse irradiation mode based on the obtained external information. The mode setting section sets the image detector to one of the pulse irradiation mode and the successive irradiation mode based on a result of determination of the determination section. The mode setting section sets the image detector to the pulse irradiation mode in a case where the image detector is allowed to be set to the pulse irradiation mode. The mode setting section sets the image detector to the successive irradiation mode in a case where the image detector is not allowed to be set to the pulse irradiation mode.

A method for controlling a radiation imaging apparatus comprises an external information obtaining step, a determining step, a mode setting step, and a controlling step. The radiation imaging apparatus is used in combination with a radiation generating apparatus, for performing fluoroscopy. The radiation generating apparatus successively generates pulses of radiation to perform pulse irradiation. The radiation imaging apparatus comprises a radiation detector and an image detector for detecting a radiation image of an object. The image detector has pixels arranged in a matrix. The each pixel stores a signal charge in accordance with a dose of the radiation. The radiation detector detects the radiation and outputs a detection signal in accordance with the dose. In the external information obtaining step, external information is obtained. The external information includes information related to the radiation generating apparatus and imaging conditions. In the determining step, whether the image detector is allowed to be set to a pulse irradiation mode is determined based on the external information. In the pulse irradiation mode, a rise and a fall of the pulse of the radiation are detected based on the detection signal outputted from the radiation detector and start timing of a storage operation for storing the signal charge is determined based on timing of detecting the rise and start timing of a readout operation for reading out the signal charge is determined based on timing of detecting the fall. In the mode setting step, the image detector is set to the pulse irradiation mode in a case where the image detector is allowed to be set to the pulse irradiation mode. The image detector is set to a successive irradiation mode in a case where the image detector is not allowed to be set to the pulse irradiation mode. In the successive irradiation mode, the storage operation and the readout operation are repeated alternately at predetermined time intervals without detection of the rise and the fall of the pulse of the radiation. In the controlling step, the image detector is controlled in one of the pulse irradiation mode and the successive irradiation mode to which the image detector is set.

According to the present invention, a radiation imaging apparatus, a method for controlling the same, and a radiation image detection device allow appropriate operation control in accordance with an irradiation profile of a radiation generating apparatus while cost increase and complicated operation are avoided, even if a radiation imaging apparatus is used in combination with a radiation generating apparatus incapable of communication, for performing the fluoroscopy.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 4 is an explanatory view illustrating an example of a determination table;

FIG. 5 is an explanatory view illustrating another example of the determination table;

DESCRIPTION OF THE PREFERRED EMBODIMENTS

Figure 1:
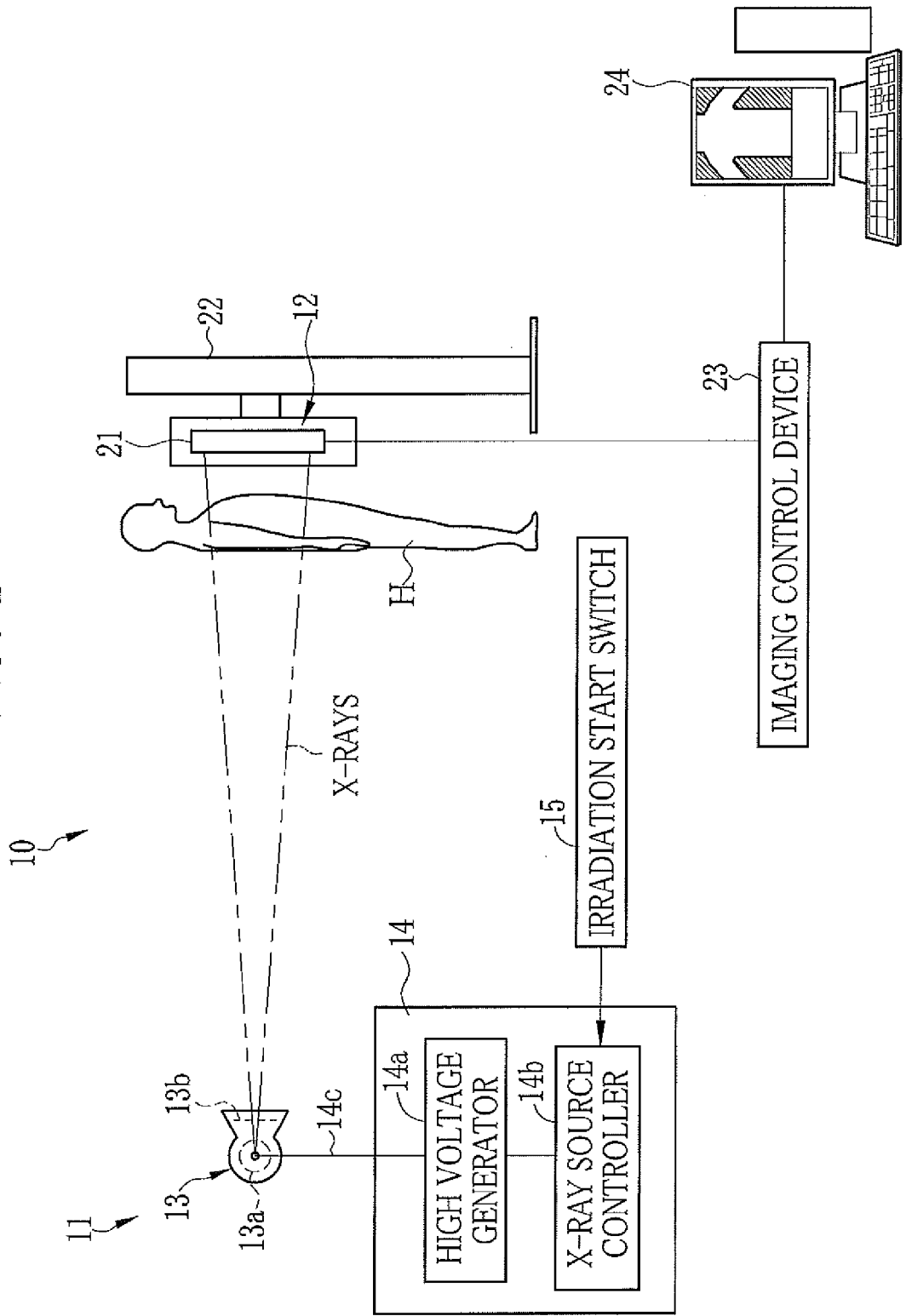
FIG. 1 is an explanatory view illustrating a schematic configuration of an X-ray imaging system.

In FIG. 1, an X-ray imaging system 10 comprises an X-ray generating apparatus 11 and an X-ray imaging apparatus 12. The X-ray generating apparatus 11 is, for example, a conventional X-ray generating apparatus employed for a film cassette or an IP cassette, and is not equipped with a communication function to communicate with the X-ray imaging apparatus 12. The X-ray generating apparatus 11 is composed of an X-ray source 13, an X-ray source control device 14 for controlling the X-ray source 13, and an irradiation start switch 15. The X-ray source 13 has an X-ray tube 13a and a collimator 13b. The X-ray tube 13a emits X-rays. The collimator 13b defines and restricts an X-ray field of the X-rays emitted from the X-ray tube 13a.

The X-ray tube 13a has a cathode and an anode (target). The cathode is composed of a filament that releases thermoelectrons. The thermoelectrons released from the cathode collide against the anode and thereby the anode emits X-rays. The collimator 13b has, for example, four lead plates that block the X-rays. The four lead plates form a rectangular emission opening through which the X-rays are transmitted. The size of the emission opening is changed by shifting the positions of the lead plates. Thereby the X-ray field is defined. The four lead plates are arranged in two pairs each composed of two lead plates opposing each other. The rectangular emission opening is formed by arranging the two pairs of lead plates orthogonal to each other.

The X-ray source control device 14 comprises a high voltage generator 14a and an X-ray source controller 14b. The high voltage generator 14a provides high voltage to the X-ray source 13. The X-ray source controller 14b controls a tube voltage, a tube current, and X-ray irradiation time. The tube voltage determines radiation quality (energy spectrum) of the X-rays emitted from the X-ray source 13. The tube current determines a radiation dose (hereinafter simply referred to as the dose) or an amount of X-ray irradiation per unit time. The high voltage generator 14a boosts an input voltage with a transformer to generate a high tube voltage, and supplies power to the X-ray source through a high voltage cable 14c. An operator such as a radiologic technologist manually operates an operation panel of the X-ray source control device 14 to set imaging conditions to the X-ray source controller 14b. The imaging conditions include a tube voltage, a tube current, X-ray irradiation time, and an imaging method. The imaging method, which is one of the imaging conditions, refers to the type of imaging, for example, still image capture or fluoroscopy. In the case where the fluoroscopy is chosen as the imaging method, note that a frame rate (fps) is also set as one of the imaging conditions.

The irradiation start switch 15 is connected to the X-ray source control device 14 through a signal cable. The irradiation start switch 15 is a two-step switch operated by the radiologic technologist. When pressed one-step, the irradiation start switch 15 generates a warm-up start signal for starting the warm-up of the X-ray source 13. When pressed two steps down, the irradiation start switch 15 generates an irradiation start signal for allowing the X-ray source 13 to start irradiation. These signals are inputted to the X-ray source control device 14 through the signal cable.

The X-ray source controller 14b controls the operation of the X-ray source 13 based on the control signal from the irradiation start switch 15. Upon receiving the irradiation start signal, generated by the irradiation start switch 15 pressed two steps down, the X-ray source controller 14b issues a start command to the X-ray source 13 and starts supplying the power to the X-ray source 13. Thereby, the X-ray source 13 starts the irradiation. During the still image capture, the X-ray source controller 14b actuates a timer at the start of supplying the power and starts measuring the X-ray irradiation time. When the irradiation time, set as one of the imaging conditions, elapses, the X-ray source controller 14b issues a stop command to the X-ray source 13 and stops supplying the power. Upon receiving the stop command, the X-ray source 13 stops the X-ray irradiation.

During the fluoroscopy, for example, upon receiving the irradiation start signal, generated by the irradiation start switch 15 through the two-step pressing, the X-ray source controller 14b issues the start commands and the stop commands alternately at a predetermined pulse period to the X-ray source 13. Thereby the X-ray source controller 14b allows the X-ray source 13 to successively emit X-ray pulses at the predetermined pulse period.

A radiographic stand 22 has a slot to which the film cassette or the IP cassette is detachably attached. The radiographic stand 22 is placed such that an X-ray incident surface of the cassette faces the X-ray source 13. Note that the radiographic stand 22, with which an image of an object (site) is captured with a subject H in a standing position, is illustrated by way of example. Instead, a radiographic table may be used to capture an image of the object with the subject H lying thereon.

The X-ray imaging apparatus 12 is composed of an X-ray image detection device 21, an imaging control device 23, and a console 24. The X-ray image detection device 21 is a portable type radiation image detection device composed of an FPD 36 (see FIG. 3) and a portable housing for accommodating the FPD 36. The X-rays emitted from the X-ray source 13 and passed through the object (site) of the subject H are incident on the X-ray image detection device 21. Thereby the X-ray image detection device 21 detects an X-ray image of the object. The X-ray image detection device 21 has a flat housing with a substantially rectangular plane. The size of the plane is substantially the same as those of the film cassette and IP cassette. Hence, the X-ray image detection device 21 fits in the radiographic stand 22.

The imaging control device 23 and the console 24 are peripheral devices of the present invention. The imaging control device 23 has a communication section and an imaging controller. The communication section communicates with the X-ray image detection device 21 and the console 24 through radio or wire. The imaging controller controls the X-ray image detection device 21 through the communication section. The imaging control device 23 transmits the imaging conditions to the X-ray image detection device 21 to allow setting of conditions for signal processing of the FPD 36. The imaging control device 23 receives the image data outputted from the X-ray image detection device 21 and transmits the image data to the console 24.

The console 24 receives input of an examination order and displays it on a display. The examination order includes information of a subject such as gender, age, a site (object) to be captured, and an imaging method. The examination order may be inputted from an external system or inputted manually by the operator such as the radiologic technologist. The external system such as HIS (Hospital Information System) or RIS (Radiation Information System) manages examination information of radiation examinations and patient information. The operator checks the contents of the examination order on the display and inputs the imaging conditions appropriate for the examination order through an operation screen of the console 24.

The console 24 transmits the imaging conditions to the imaging control device 23. The console 24 performs various image processes such as gamma correction and frequency processing on the data of an X-ray image transmitted from the imaging control device 23. After the image processes, the X-ray image is displayed on the display of the console 24. The data of the X-ray image is stored in a hard disk or a memory of the console 24, or a data storage device such as an image storage server connected to the console 24 through a network.

Information related the X-ray generating apparatus 11 is registered into the imaging control device 23. The X-ray generating apparatus 11 is used in combination with the X-ray image detection device 21. The "information related to the X-ray generating apparatus 11" is the information related to a type of the X-ray tube 13a, for example, a diode, a triode, or a tetrode. The type of the X-ray tube 13a is identified by the manufacturer name, the product name, the model number, the specification information, or the like. A service person or an operator registers the type(s) of the X-ray tube(s) 13a at the time of installation of the X-ray imaging apparatus 12 or maintenance thereof.

The console 24 has a function to display a select screen. The console 24 reads the types of the X-ray tubes 13a from the imaging control device 23 and displays them on the select screen, and allows the operator to choose one of the types of the X-ray tubes 13a to be used. Through the select screen, the operator chooses the type of the X-ray tube 13a to be used in combination with the X-ray image detection device 21, and thereby the type of the X-ray tube 13a chosen is inputted to the console 24. The console 24 transmits the type of the X-ray tube 13a to the imaging control device 23. The imaging control device 23 transmits the type of the X-ray tube 13a and the imaging conditions to the X-ray image detection device 21.

The type of the X-ray tube 13a, the frame rate (fps) included in the imaging conditions of the fluoroscopy, a tube current and a tube voltage supplied to the X-ray tube 13a are referred to as external information. The external information is a factor which determines an irradiation profile of the X-rays (hereinafter simply referred to as the irradiation profile) in a case where the X-ray generating apparatus 11 performs pulse irradiation. To be more specific, the external information determines an overlapping state of a rising edge and a falling edge of the two successive X-ray pulses during the pulse irradiation. The external information is used to set an operation mode of the X-ray image detection device 21 in the fluoroscopy, which will be described below.

Figure 2:
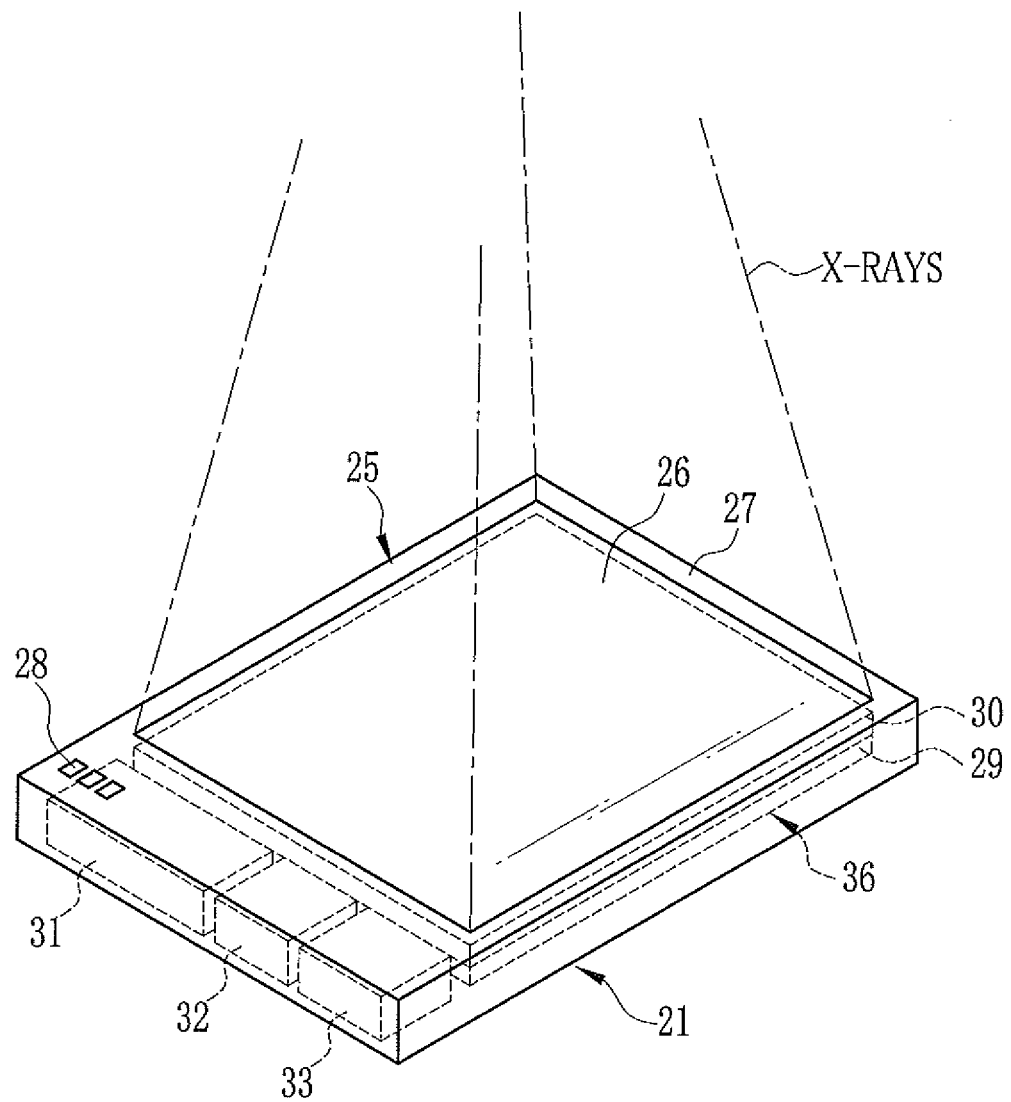
FIG. 2 is an external perspective view of an X-ray image detection device.

As shown in FIG. 2, the X-ray image detection device 21 comprises a housing 25. A rectangular area on the top face of the housing 25 is an X-ray incident surface. The housing 25 is composed of a top plate 26 and a housing body 27 having the components other than the top plate 26. The top plate 26 comprises the X-ray incident surface. For example, the top plate 26 is made from carbon. The housing body 27 is made from metal, resin, or the like. Thereby the X-ray absorption by the top plate 26 is inhibited while the strength of the housing body 27 is reinforced.

An indicator 28 is provided on the top face of the housing 25. The indicator 28 notifies the operator of an operating state or the like of the X-ray image detection device 21. The indicator 28 is composed of, for example, two or more light emitting sections. The operating state of the X-ray image detection device 21, a battery level (a remaining amount of the battery), and the like are displayed by the combination of the emissions of the light emitting sections. The operating states include, for example, "ready" representing a standby state for image capture, "transmission" representing that image data is being transmitted after the image capture, and the like. The indicator 28 may be a display device such as an LCD.

In the housing 25 of the X-ray image detection device 21, the FPD 36 is disposed to face the X-ray incident surface. The FPD 36 detects X-ray images. The FPD 36 is an indirect conversion type comprising a scintillator 29 and a detection panel 30. The scintillator 29 converts the X-rays into visible light. The detection panel 30 photoelectrically converts the visible light converted by the scintillator 29. The FPD 36 employs an "ISS (Irradiation Side Sampling) system" in which the detection panel is disposed on the X-ray incident surface side of the scintillator 29. Note that the FPD 36 may employ a "PSS (Penetration Side Sampling) system" in which the positions of the scintillator 29 and the detection panel 30 are reversed from those in the ISS system.

Inside the housing 25, various electronic circuits 31, a battery 32, and a communicator 33 are disposed along one of short sides of the X-ray incident surface. The electronic circuits 31 are used for controlling the FPD 36. A material with X-ray shielding properties protects the electronic circuits 31 from damage due to the incident X-rays. The battery 32 is incorporated in the housing 25 in a rechargeable and detachable manner. The battery 32 supplies the power to the FPD 36, the electronic circuits 31, and the communicator 33. The communicator 33 communicates with the imaging control device 23 through radio or wire.

Figure 3:
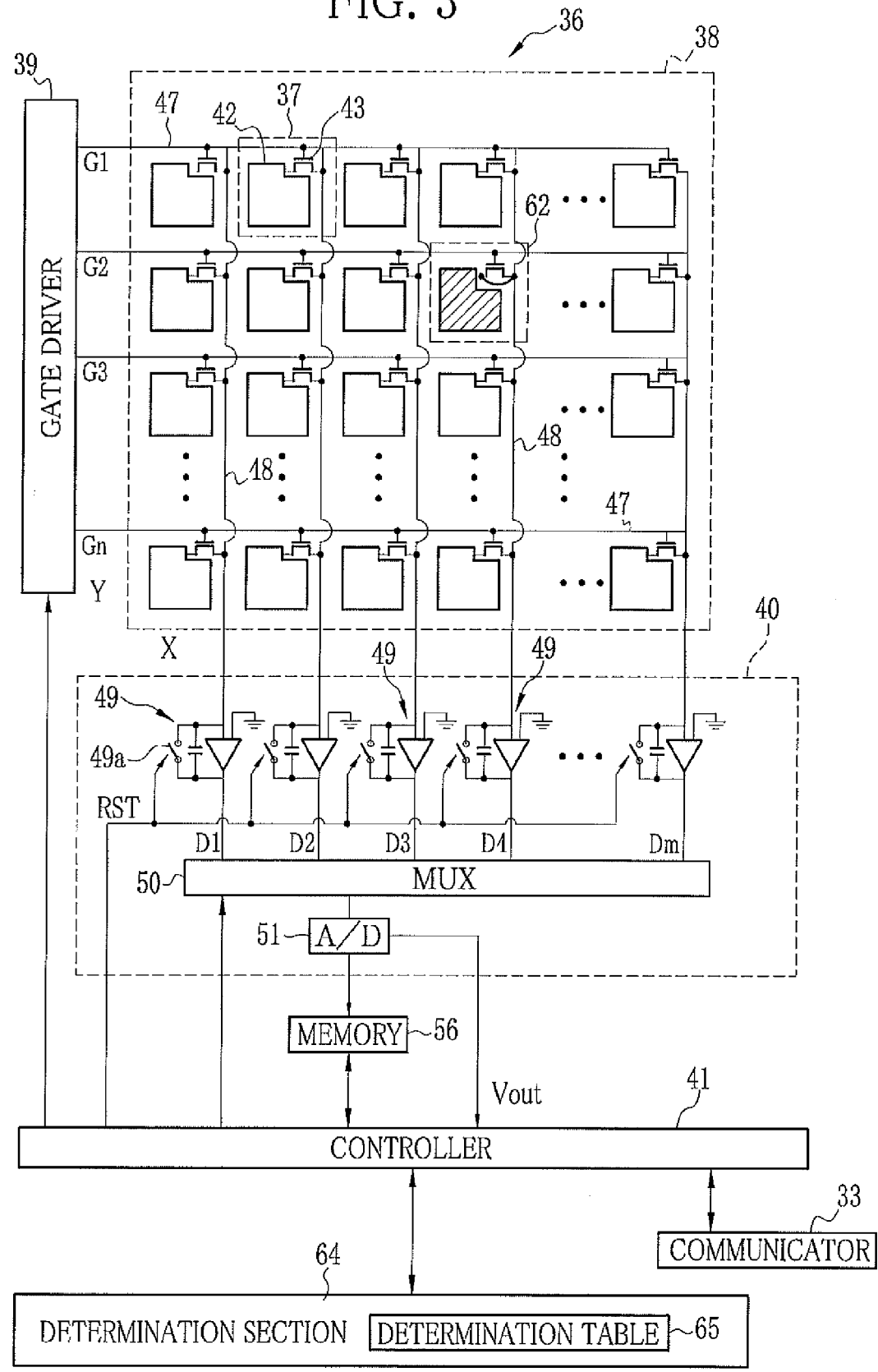
FIG. 3 is an explanatory view illustrating configuration of an FPD.

In FIG. 3, the FPD 36 comprises the detection panel 30, a gate driver 39, a signal processing circuit 40, and a controller 41. The detection panel 30 has a TFT active matrix substrate on which an image capture field 38 is formed. The image capture field 38 is composed of pixels 37 in an array on the TFT active matrix substrate. Each pixel 37 stores a signal charge in accordance with an amount of the incident X-rays. The gate driver 39 drives the pixels 37 and controls reading of the signal charges. The signal processing circuit 40 converts the signal charges, read out from the pixels 37, into digital data and outputs the digital data. To control the FPD 36, the controller 41 controls the gate driver 39 and the signal processing circuit 40. The communicator 33 is connected to the controller 41. The communicator 33 communicates with the imaging control device 23 through radio or wire. The communicator 33 obtains the external information, which includes the type of the X-ray tube 13a and the imaging conditions inputted from the console 24. The pixels 37 are arranged in two dimensions in a matrix of n rows (x direction)×m columns (y direction) at a predetermined pitch.

The FPD 36 has the scintillator 29 (see FIG. 2) that converts the incident X-rays into visible light. The FPD 36 is an indirect conversion type that photoelectrically converts the visible light, converted by the scintillator 29, with the pixels 37. The scintillator 29 is disposed to face the whole image capture field 38 in which the pixels 37 are arranged. The scintillator 29 is made from phosphor such as CsI (cesium iodide) or GOS (gadolinium oxysulfide). Note that an FPD of a direct conversion type may be used instead. The direct conversion type FPD has a conversion layer (amorphous selenium or the like) for directly converting the X-rays into charges.

Each pixel 37 has a photodiode 42, a capacitor (not shown), and a thin film transistor (TFT) 43. The photodiode 42 is a photoelectric conversion element that generates a charge (electron-hole pair) due to the incidence of visible light. The capacitor stores the charge generated by the photodiode 42. The TFT 43 is a switching element.

The photodiode 42 has a semiconductor layer (for example, a PIN type) made from a-Si (amorphous silicon) or the like. An upper electrode and a lower electrode are disposed on the top and the bottom of the semiconductor layer, respectively. The TFT 43 is connected to the lower electrode. A bias line (not shown) is connected to the upper electrode.

A bias voltage is applied to the upper electrode of the photodiode 42 of each pixel 37 in the image capture field 38 through the corresponding bias line. The application of the bias voltage produces an electric field in the semiconductor layer of the photodiode 42. The charge (electron-hole pair) is generated in the semiconductor layer by the photoelectric conversion. The negative electrons and the positive holes are attracted to the upper and lower electrodes with positive and negative polarities, respectively. Thereby, the charge is stored in the capacitor.

A gate electrode of the TFT 43 is connected to a scanning line 47. A source electrode of the TFT 43 is connected to a signal line 48. A drain electrode of the TFT 43 is connected to the photodiode 42. The scanning lines 47 and the signal lines 48 are arranged in a lattice shape. The number of the scanning lines 47 coincides with the number "n" of the rows of the pixels 37 arranged in the image capture field 38. The pixels 37 of each row are connected to the corresponding scanning line 47. The number of the signal lines 48 coincides with the number "m" of the columns of the pixels 37. The pixels 37 of each column are connected to the corresponding signal line 48. The scanning lines 47 are connected to the gate driver 39. The signal lines 48 are connected to the signal processing circuit 40.

The gate driver 39 drives the TFTs 43 to carry out a storage operation, a readout operation, or a reset operation. In the storage operation, each pixel 37 stores the signal charge corresponding to the amount of the incident X-rays. In the readout operation, the signal charge is read out from the pixels 37. In the reset operation, the charges stored in the pixels 37 are discharged. The controller 41 controls the start timing of each of the above operations through the gate driver 39.

During the storage operation, the TFT 43 is in an OFF state and the signal charge is stored in the pixel 37. During the readout operation, the gate driver 39 generates gate pulses G1 to Gn sequentially. The gate pulses G1 to Gn sequentially drives the respective scanning lines 47 one by one. Each gate pulse activates the corresponding scanning line 47 and thereby drives the TFTs 43 connected to the activated scanning line 47 at a time. Thus, the TFTs 43 are turned ON on a row-by-row basis.

When the TFTs 43 of a single row are turned on, the signal charges stored in the pixels 37 of the row are inputted to the signal processing circuit 40 through the respective signal lines 48. In the signal processing circuit 40, the signal charges of the row are converted into voltages and outputted. The output voltages corresponding to the signal charges of the respective signal lines are readout as voltage signals D1 to Dm. The analog voltage signals D1 to Dm are converted into digital data. Thereby image data is produced. The image data is digital pixel values representing concentration of the pixels of the row. The image data is outputted to a memory 56 incorporated inside the housing of the X-ray image detection device 21.

A dark current occurs in the semiconductor layer of the photodiode 42, regardless of the presence or absence of the incident X-rays. A dark charge, which occurs in accordance with the dark current, is stored in the capacitor because the bias voltage is applied. The reset operation is performed to remove the dark charge, being a noise component to the image data. The reset operation is to discharge the dark charge from each pixel 37 through the corresponding signal line 48.

The reset operation is performed using a sequential reset method in which the pixels 37 are reset on a row-by-row basis, for example. In the sequential reset method, the gate driver 39 issues the gate pulses G1 to Gn to the respective scanning lines 47 sequentially and thereby the TFTs 43 of the pixels 37 are turned on from row to row, in a manner similar to the readout operation of the signal charges. While the TFTs 43 are turned on, the dark charges from the pixels 37 are inputted to the signal processing circuit 40 through the corresponding signal lines 48.

In the reset operation, unlike the readout operation, the output voltage corresponding to the dark charge is not read out from the signal processing circuit 40. Instead, the controller 41 outputs the reset pulses RST, in synchronization with the generation of the gate pulses G1 to Gn, to the signal processing circuit 40. When the reset pulse RST is inputted to the signal processing circuit 40, a reset switch 49a of an integrating amplifier 49, which will be described below, is turned on and thereby the inputted dark charge is discharged.

Instead of the sequential reset method, a parallel reset method or an entire reset method may be used. In the parallel reset method, two or more rows of the pixels are treated as a group. The sequential reset is performed within each group. Then the dark charges of the rows of the number of the groups are discharged simultaneously. In the entire reset method, the gate pulses are inputted to all the rows at a time, so that the dark charges of all the pixels are discharged simultaneously. The reset operation is accelerated by using the parallel reset method or the entire reset method.

The signal processing circuit 40 is composed of integrating amplifiers 49, a MUX 50, an A/D converter 51, and the like. The integrating amplifiers 49 are connected to the signal lines 48, respectively. The integrating amplifier 49 is composed of an operational amplifier and a capacitor connected between an input and output terminals of the operational amplifier. The signal line 48 is connected to one of the input terminals of the operational amplifier. The other input terminal (not shown) of the integrating amplifier 49 is connected to the ground (GND). The integrating amplifiers 49 integrate the signal charges inputted from the signal lines 48, and converts them into the voltage signals D1 to Dm, respectively, and outputs them.

The output terminal of the integrating amplifier 49 of each column is connected to the MUX 50 through an amplifier (not shown) or a sample hold section (not shown). The amplifier amplifies the voltage signals D1 to Dm. The sample hold section holds the voltage signals D1 to Dm. The MUX 50 chooses one of the integrating amplifiers 49 connected in parallel, and inputs one of the voltage signals D1 to Dm, outputted from the chosen integrating amplifier 49, to the A/D converter 51, in a serial manner. The A/D converter 51 converts the analog voltage signals D1 to Dm into digital pixel values in accordance with their signal levels.

After the storage operation, in the readout operation in which the signal charges are read out, the gate pulse turns on the TFTs 43 on a row-by-row basis. The signal charges stored in the pixels 37 of a row are inputted to the integrating amplifiers 49 through the signal lines 48, respectively.

When the integrating amplifiers 49 output the voltage signals D1 to Dm of a single row, the controller 41 outputs the reset pulse (reset signal) RST to each integrating amplifier 49. Thereby the reset switch 49a of each integrating amplifier 49 is turned on. Thus, the signal charges of the row, stored in the integrating amplifiers 49, are discharged. When the integrating amplifiers 49 are reset, the gate driver 39 outputs the gate pulse to the next row. Thereby the signal charges of the pixels 37 of the next row are read out. These steps are repeated sequentially to read out the signal charges of the pixels 37 of each row.

After the signal charges are read out from every row, the image data representing an X-ray image of one screen is recorded in the memory 56. Image correction processes are performed on the image data stored in the memory 56. The image correction processes include offset correction and sensitivity correction. In the offset correction, an offset component, which is a fixed pattern noise due to an individual difference or environment of the FPD 36, is removed. In the sensitivity correction, variations in sensitivities of the photodiodes 42 of the pixels 37 and variations in output characteristics of the signal processing circuit 40 are corrected. The image data is read out from the memory 56 and outputted to the imaging control device 23, and then transmitted to the console 24. Thus, the X-ray image of the object is detected.

The FPD 36 has a synchronous control function using a self detection method. In the self detection method, the FPD 36 self-detects the irradiation timing of the X-ray source 13 and synchronizes the operation of the FPD 36 with the detected irradiation timing, without transmission of a synchronization signal between the X-ray generating apparatus 11 and the FPD 36. As shown by a portion with hatch lines in FIG. 3, a short-circuited pixel 62 is provided in the image capture field 38 of the PFD 36. The short-circuited pixel 62 is a detection element for detecting the timing of the start and the end of the X-ray irradiation. The TFT 43 turns on/off the electrical connection between the pixel 37 and the signal line 48. On the other hand, the short-circuited pixel 62 is always kept short-circuited with the signal line 48.

The configuration of the short-circuited pixel 62 is substantially the same as that of the pixel 37. Each short-circuited pixel 62 has the photodiode 42 and the TFT 43. The photodiode 42 generates the signal charge in accordance with the dose. The short-circuited pixel 62 differs from the pixel in that the source and the drain of the TFT 43 are short-circuited through a connection. Namely, the TFT 43 of the short-circuited pixel 62 does not have the switching function. Thereby the signal charge generated in the photodiode 42 of the short-circuited pixel 62 is constantly transmitted through the signal line 48 to the integrating amplifier 49. Note that, instead of connecting the source and the drain of the TFT 43, the photodiode 42 of the short-circuited pixel 62 may be directly connected to the signal line 48 without the use of the TFT 43.

The controller 41 measures the X-ray intensity (the dose per unit time) of the X-rays incident on the FPD 36 from the X-ray source 13, based on the output from the short-circuited pixel 62. Thereby the controller 41 monitors a change in X-ray intensity. With the use of the MUX 50, the controller 41 chooses the integrating amplifier 49 to which the signal charge is inputted from the short-circuited pixel 62. The controller 41 reads out the voltage signal, being the output voltage Vout of the short-circuited pixel 62, from the integrating amplifier 49. The controller 41 resets the integrating amplifier 49 each time the controller 41 reads out the output voltage Vout. During the storage operation, the controller 41 repeats the operation of reading out the output voltage Vout at very short time intervals relative to the X-ray irradiation time, so as to monitor a change in the X-ray intensity of the X-rays being emitted.

The controller 41 converts a value of the output voltage Vout into digital data and records it in the memory 56. The controller 41 monitors a change in the X-ray intensity of the X-rays emitted from the X-ray source 13, based on a change with time in the output voltage Vout recorded in the memory 56. To perform the synchronous control using the self detection method (hereinafter simply referred to as the synchronous control), the controller 41 detects a rise and a fall of the X-ray pulse, based on the change in the output voltage Vout with time and thereby the controller 41 detects timing of the start and the end of the X-ray irradiation. In the case of the still image capture, the FPD 36 performs the synchronous control. The storage operation is started in accordance with the start of the X-ray irradiation. The storage operation is ended in accordance with the end of the X-ray irradiation and then the readout operation is performed.

For the fluoroscopy, the FPD 36 has two operation modes: a pulse irradiation mode corresponding to pulsed X-ray irradiation from the X-ray source 13 and a successive irradiation mode corresponding to successive X-ray irradiation at a substantially constant intensity from the X-ray source 13. In the pulse irradiation mode, the FPD 36 performs synchronous control using a self detection method, with which the FPD 36 self-detects the rises and the falls of the successive X-ray pulses to detect timing of each of the start and the end of the X-ray irradiation, in a manner similar to the still image capture. The X-ray source 13 performs the pulse irradiation at a predetermined pulse period. There may be a slight shift in the timing of the rises and the falls of the successive X-ray pulses, resulting in a fluctuation in the pulse period. The synchronous control using the self detection method accurately synchronizes the operation of the FPD 36 with the pulsed X-ray irradiation even if a fluctuation occurs in the pulse period.

In the successive irradiation mode, the storage operation and the readout operation are repeated alternately at predetermined time intervals during the successive X-ray irradiation. Because the X-ray intensity is substantially constant throughout the successive X-ray irradiation, the FPD 36 repeats the storage operation and the readout operation alternately at the predetermined time intervals without taking the synchronization into account.

Basically, the FPD 36 is set to the pulse irradiation mode or the successive irradiation mode based on whether the X-ray source 13 performs the pulse irradiation or the successive irradiation. However, there are cases in which the synchronous control is impossible, depending on the irradiation profile of the pulse irradiation as shown in FIG. 13 by way of example. The irradiation profiles shown in FIGS. 12 and 13 have the same pulse width and the same wave-tail duration Ts, but differ in pulse period. In a case where a pulse period PP (denoted as PP1 in FIG. 12) of the X-ray pulse is long as shown by the irradiation profile in FIG. 12, there is no overlap between the successive two X-ray pulses and the valley between the two X-ray pulses is distinct. Thereby, the synchronous control is allowed.

On the other hand, in a case where a pulse period PP (denoted as PP2 in FIG. 13) of the X-ray pulse is short as shown by the irradiation profile in FIG. 13, two successive X-ray pulses overlap each other, which makes the valley between the pulses indistinct. In this case, the synchronous control is impossible. To be more specific, the rise and the fall of the X-ray pulse cannot be detected unless the X-ray intensity at the valley between the two X-ray pulses is less than or equal to a threshold voltage Vth in the irradiation profile. For this reason, the synchronous control is impossible.

The FPD 36 has a mode setting function to automatically determine whether the synchronous control is allowed, based on the above-described external information, in a case where the X-ray source 13 performs the pulsed X-ray irradiation and to set its operation mode in accordance with the result of the determination. In a case where the synchronous control is allowed, the FPD 36 is set to the pulse irradiation mode. Otherwise, the FPD 36 is set to the successive irradiation mode. Because of the overlap between the two successive X-ray pulses, the irradiation profile shown in FIG. 13 becomes similar to an irradiation profile of the successive irradiation with the substantially constant X-ray intensity. For this reason, the FPD 36 operates in the successive irradiation mode even if the X-ray source 13 performs the pulsed X-ray irradiation.

In the FPD 36, a determination section 64, connected to the controller 41, refers to a determination table 65 or checks the external information against the determination table 65 to determine whether the pulse irradiation mode is allowed, based on the external information transmitted from the imaging control device 23. The determination section 64 functions as a mode setting section for setting the operation mode of the FPD 36 based on the result of the determination in a determination process. The determination section 64 sets the FPD 36 to the pulse irradiation mode in a case where the determination section 64 determines that the pulse irradiation mode is allowed. The determination section 64 sets the FPD 36 to the successive irradiation mode in a case where the determination section 64 determines that the pulse irradiation mode is not allowed.

In the determination table 65, information of whether the pulse irradiation mode is allowed is recorded per combination of a tube current and a frame rate, for example. Two or more determination tables 65 are provided for each type of the X-ray tube 13a. The determination section 64 selects the determination table 65 corresponding to the type of the X-ray tube 13a specified in the external information. FIG. 4 shows the determination table 65 for a diode, for example, an X-ray tube α. In the determination table 65, the tube current increases from $I_1$ to $I_n$ in this order. The frame rate also increases from $F_1$ to $F_n$ in this order. Each of "A" and "B" denotes an evaluation of whether the pulse irradiation mode is allowed or not: "A" denotes that the pulse irradiation mode is allowed; "B" denotes that the pulse irradiation mode is not allowed.

The results "A" and "B" on the determination table 65 are evaluated based on the time necessary for the dose to be reduced to "0" after the X-ray irradiation is ended. Namely, the results "A" and "B" are evaluated based on the duration of the wave tail of the X-ray pulse and the frame rate (the pulse period of the X-ray pulse). The duration of the wave tail is calculated using a time constant τ representing a falling state of the dose after the irradiation is ended. After the end of the X-ray irradiation, the dose, obtained in accordance with the tube current and the tube voltage, decreases exponentially with the time constant τ. It is known that the time of three to five times the time constant τ is necessary for the dose to be reduced to "0". For example, in a case where the X-ray tube 13a is considered as a resistance R, an equation R=V/I is satisfied where "I" denotes a tube current and "V" denotes a tube voltage. In a case where $C_{Tube}$ [pF] denotes a capacity of the X-ray tube 13a, $C_{Line}$ [pF/m] denotes a capacity of the high voltage cable 14c that connects the X-ray tube 13a and the high voltage generator 14a, and "L" denotes the cable length of the high voltage cable 14c, a capacity "C" that is the sum of the capacity of the X-ray tube 13a and the capacity of the high voltage cable 14c is calculated by $C=C_{Tube}+C_{Line}\times L$. Hence, the time constant τ is calculated by $\tau=RC=V/I(C_{Tube}+C_{Line}\times L)$.

Examples of specific values of parameters for calculating the time constant τ are as follows: the capacity $C_{Tube}$ of the X-ray tube 13a is 500 to 1000 [pF]; the capacity $C_{Line}$ of the high voltage cable 14c is 100 to 200 [pF/m]; the cable length L of the high voltage cable 14c is 10 to 20 [m]; the tube voltage V is 50 to 150 [kV]; the tube current I is 0.5 to 20 [mA]. The time constant τ calculated using these values of the parameters is in the order of several ms to several tens ms.

As described above, the wave tail of the X-ray pulse varies depending on the capacity C that is the sum of the capacity of the X-ray tube 13a and the capacity of the high voltage cable 14c, the tube current I, and the tube voltage V. For example, the wave tail elongates as the capacity C increases or the tube current I decreases or the tube voltage V increases. The pulse period PP of the X-ray pulse shortens as the frame rate increases. Hence, an overlapping state of the two X-ray pulses is assumed from the duration of the wave tail of the X-ray pulse and the frame rate. Thereby whether the pulse irradiation mode is allowed is determined.

Figure 12:
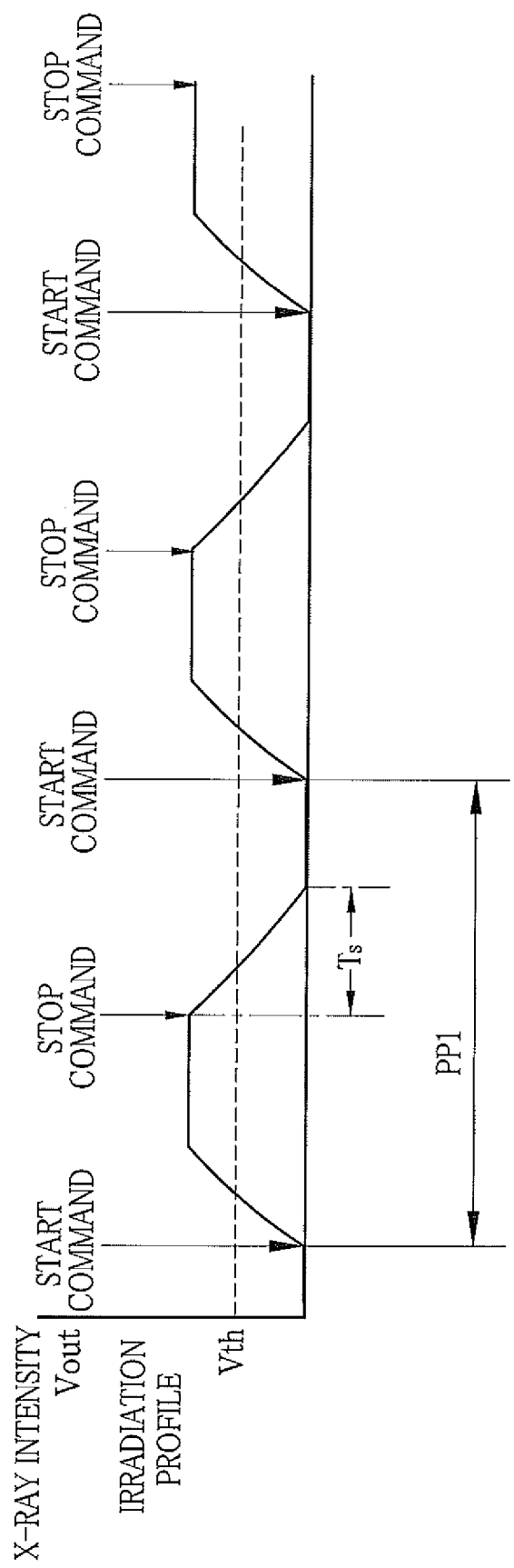
FIG. 12 is an explanatory view illustrating an irradiation profile in a case where there is no overlap between the X-ray pulses.
Figure 13:
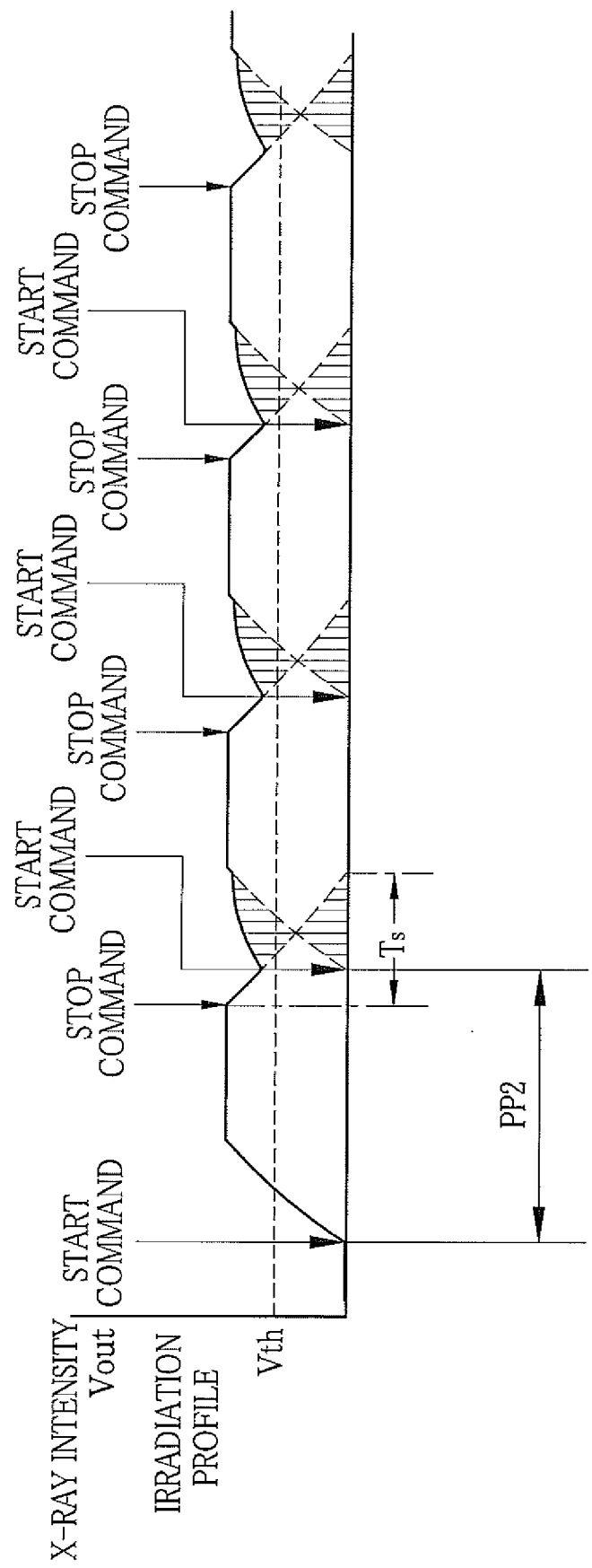
FIG. 13 is an explanatory view illustrating an irradiation profile in a case where the X-ray pulses overlap each other.

For example, as shown in FIG. 12, in a case where the frame rate is relatively low and the pulse period PP1 is relatively long, the wave tail of the preceding X-ray pulse and the rising edge of the subsequent X-ray pulse do not overlap each other even if the duration of the wave tail of the X-ray pulse is long. A valley between the two successive X-ray pulses is distinct. The X-ray intensity is less than the threshold voltage Vth at the valley between the two pulses. Consequently the rises and the falls of the X-ray pulses are detected surely. The determination table 65 evaluates the state shown in FIG. 12 as "A" meaning that the FPD 36 is allowed to be set to the pulse irradiation mode.

Conversely to the above, as shown in FIG. 13, in a case where the frame rate is relatively high and the pulse period PP2 is relatively short, the wave tail of the preceding X-ray pulse overlaps the rising edge of the subsequent X-ray pulse if the duration of the wave tail of the X-ray pulse is long. The peak of the X-ray pulse and the valley between the X-ray pulses become indistinct, so that the rise and the fall of the X-ray pulse cannot be detected. The determination table 65 evaluates the state shown in FIG. 13 as "B" meaning that the FPD 36 is not allowed to be set to the pulse irradiation mode.

As shown in the determination table 65 for the diode in FIG. 4, in a case where the tube current is low ("$I_1$"), each evaluation is "B" regardless of the frame rate because the duration of the wave tail of the X-ray pulse is relatively long. Hence, in the case where the tube current is $I_1$, the determination section 64 sets the FPD 36 to the successive irradiation mode. The evaluation is "A" in a case where the tube current is $I_2$ and the frame rate is $F_1$, so that the FPD 36 is set to the pulse irradiation mode. However, in a case where the frame rate is greater than or equal to $F_2$, the X-ray pulse period PP is relatively short, so that the evaluation is "B". Thus, the determination section 64 sets the FPD 36 to the pulse irradiation mode in the case where the tube current is $I_2$ and the frame rate is $F_1$. The determination section 64 sets the FPD 36 to the successive irradiation mode in the case where the tube current is $I_2$ and the frame rate is greater than or equal to $F_2$. Note that, for each of the tube currents $I_3$ to $I_n$, whether the pulse irradiation mode is allowed is evaluated based on the relationship with the frame rate, in a manner similar to the tube currents $I_1$ and $I_2$.

FIG. 5 shows a determination table 68 for an X-ray tube β (triode) by way of example. Because the response speed of the X-ray tube β (triode) is faster than that of the X-ray tube α (diode), a range for the pulse irradiation mode, allowed to the X-ray tube β, is greater than that allowed to the X-ray tube α. For this reason, in a case where the X-ray tube β is used, the evaluation is "A" at the frame rate $F_1$ even with the low tube current $I_1$. In this case, the FPD 36 is set to the pulse irradiation mode. In addition, in a case where the tube current is $I_2$, the FPD 36 is set to the pulse irradiation mode at the frame rate of $F_1$ and $F_2$. For the tube currents $I_3$ to $I_n$, the range for the pulse irradiation mode, allowed to the X-ray tube β, is greater than that allowed to the X-ray tube α, in a manner similar to the tube currents $I_1$ and $I_2$.

As described above, the duration Ts of the wave tail of the X-ray pulse varies with the tube current and the tube voltage, set at each image capture, even if the pulsed X-ray irradiation is performed using the same X-ray tube at the same pulse period. Hence, the X-ray pulses may or may not overlap each other depending on the duration Ts of the wave tail. Even if the pulsed X-ray irradiation is performed at the same pulse period, the same tube current, and the same tube voltage, the X-ray pulses may or may not overlap each other because the response speed varies depending on the type of the X-ray tube. The overlapping state of the X-ray pulses demonstrates the following tendencies, depending on the combination of the type of the X-ray tube, the tube current, and the frame rate.

For example, in a case where the tube current is high (in other words, the duration of the wave tail of the X-ray pulse is relatively short) and the frame rate is low (in other words, the pulse period of the X-ray pulse is relatively long), the FPD 36 is likely to be set to the pulse irradiation mode. In a case where the tube current is low (in other words, the duration of the wave tail of the X-ray pulse is relatively long) and the frame rate is low (in other words, the pulse period of the X-ray pulse is relatively long), the result of the determination of whether the pulse irradiation mode is allowed varies depending on the type of the X-ray tube 13a. To be more specific, the pulse irradiation mode is not likely to be allowed in a case where the X-ray tube 13a is a diode with a slow response speed. In a case where the X-ray tube 13a is a triode or a tetrode, a range for the pulse irradiation mode, allowed to the triode or the tetrode, is greater than that allowed to the diode because the response speed of the triode or the tetrode is faster than that of the diode. In a case where the frame rate is high (in other words, the pulse period of the X-ray pulse is relatively short), the pulse irradiation mode is not likely to be allowed regardless of the tube current. This is because the two X-ray pulses overlap each other as shown in FIG. 13 in the case where the tube current is low (in other words, the duration of the wave tail is relatively long). Even in the case where the tube current is high (in other words, the duration of the wave tail is relatively short), the self detection cannot be performed in a case where the frame rate is extremely high.

Note that, in a case where the external information does not include the information related to the type of the X-ray tube 13a, the determination section 64 does not determine whether the pulse irradiation mode is allowed, but sets the FPD 36 to the successive irradiation mode.

The controller 41 sets time (storage operation time) for storage operation when setting the FPD 36 to the successive irradiation mode. The controller 41 calculates the pulse period PP from the frame rate. The controller 41 sets the storage operation time based on the pulse period PP. It is preferable that the storage operation, the readout operation, and the reset operation are performed during the pulse period PP. The controller 41 subtracts the time necessary for the reset operation and the readout operation from the pulse period PP to get the storage operation time, for example.

Hereinafter, referring to FIGS. 6 and 7, a flowchart in FIG. 10, FIGS. 8 and 9, and a timing chart in FIG. 11, an operation of the above configuration is described. In a case where an image is captured using the X-ray imaging system 10, first, a position of a site (object) of the subject H to be captured and an irradiation position of the X-ray source 13 are determined relative to the position of the radiographic stand 22 to which the X-ray image detection device 21 is set. The examination order and the imaging conditions based on the imaging order are inputted to the console 24. The examination order includes the gender, the age, and the site to be captured of the subject H, and the imaging method. The imaging conditions include the tube current and the tube voltage. In a case where the imaging method is the fluoroscopy, the frame rate is inputted. The information related to the type of the X-ray tube 13a used by the operator is also inputted to the console 24.

The information related to the imaging conditions and the information related to the type of the X-ray tube 13a is transmitted from the console 24 to the imaging control device 23. The imaging control device 23 transmits the imaging conditions to the X-ray image detection device 21 to allow the X-ray image detection device 21 to set the signal processing conditions of the FPD 36. The imaging control device 23 transmits the type of the X-ray tube 13a inputted. The operator sets the imaging conditions to the X-ray source 13 based on the imaging conditions inputted to the console 24.

The determination section 64 of the X-ray image detection device 21 checks whether the imaging method, included in the imaging conditions, is the fluoroscopy or not (S001). In a case where the imaging method is to capture a still image, the determination section 64 sets the FPD 36 to the pulse irradiation mode (N in S001). In a case where the imaging method is the fluoroscopy (Y in S001), the determination section 64 checks the type of the X-ray tube 13a on the external information (S002). In a case where the external information does not have the information related to the type of the X-ray tube 13a (N in S002), the determination section 64 sets the FPD 36 to the successive irradiation mode (S003). In a case where the FPD 36 is set to the successive irradiation mode, the controller 41 sets the storage time of the FPD 36 based on the frame rate (S004).

In a case where the external information has the information related to the type of the X-ray tube 13a (Y in S002), the determination section 64 selects the determination table 65, 68, or the like corresponding to the type of the X-ray tube 13a. The determination section 64 refers to the selected determination table and determines whether the pulse irradiation mode is allowed (S005). The determination section 64 reads information related to the evaluation as to whether the pulse irradiation mode is allowed, based on the combination of the type of the X-ray tube 13a, and the frame rate and the tube current which are read out from the imaging conditions. Upon determining that the FPD 36 is allowed to be set to the pulse irradiation mode (Y in S006), the determination section 64 sets the FPD 36 to the pulse irradiation mode (S007). Upon determining that the FPD 36 is not allowed to be set to the pulse irradiation mode (N in S006), based on the combination of the type of the X-ray tube 13a, the frame rate, and the tube current, the determination section 64 sets the FPD 36 to the successive irradiation mode (S003). In this case, the controller 41 sets the storage time of the FPD 36 based on the frame rate (S004).

Figure 7:
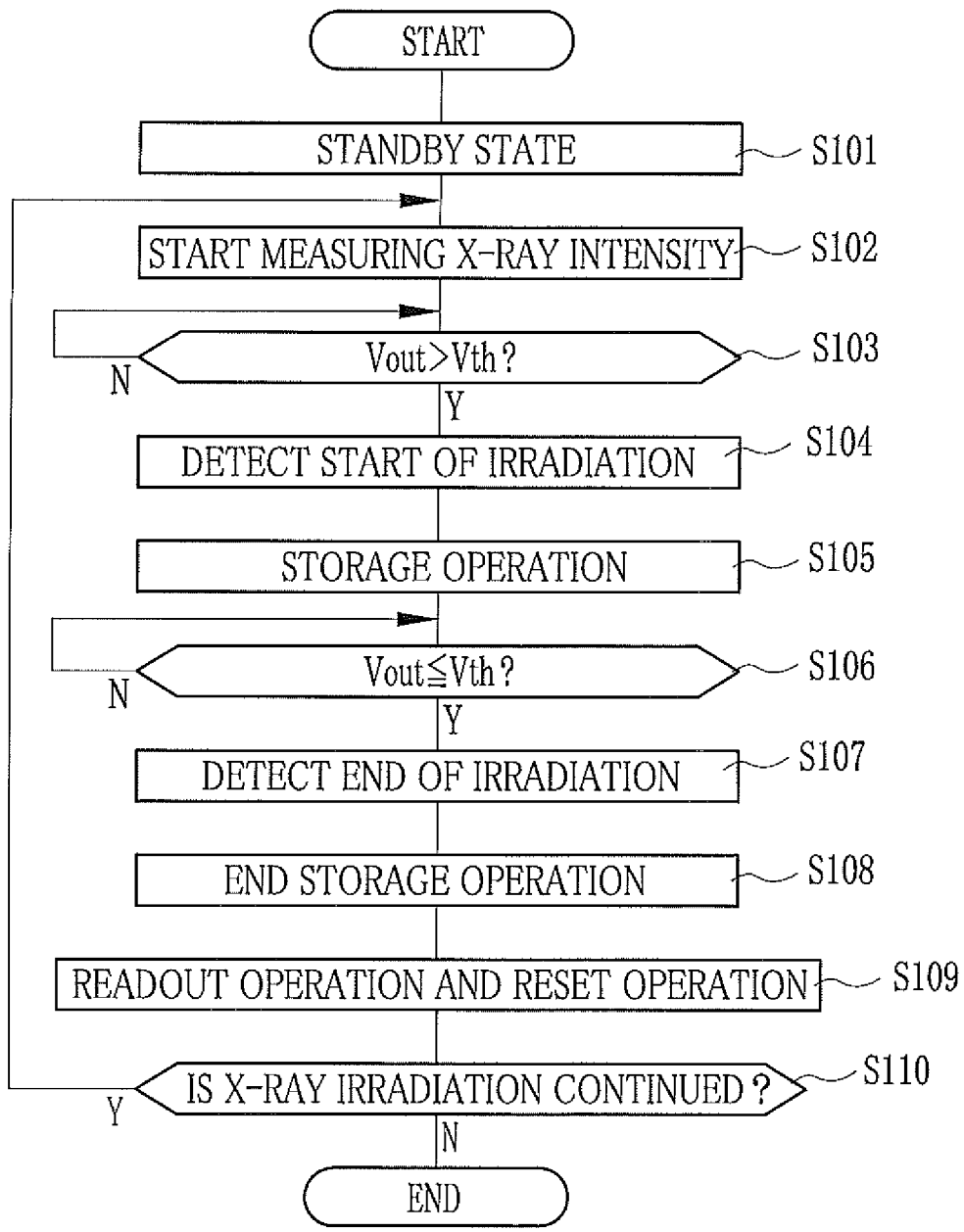
FIG. 7 is a flowchart illustrating steps for controlling the FPD in a pulse irradiation mode.
Figure 8:
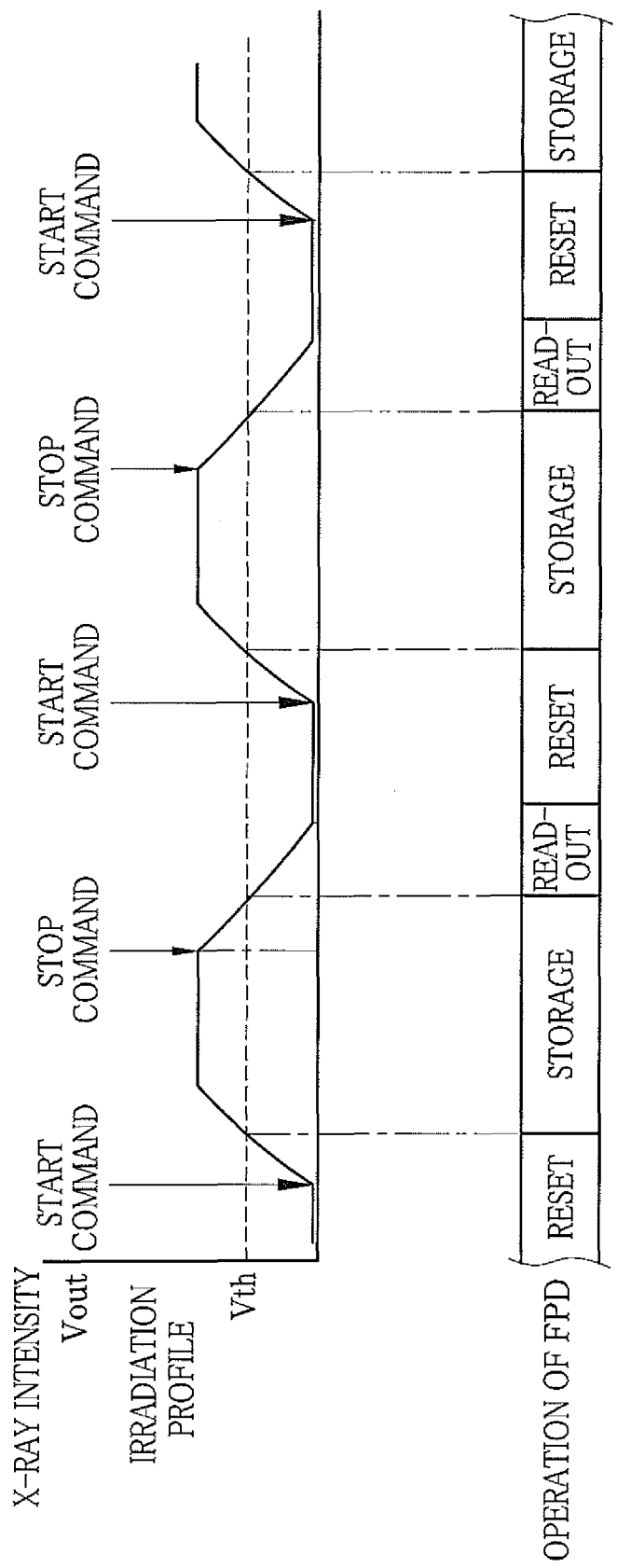
FIG. 8 is an explanatory view illustrating an irradiation profile and operations of the FPD in a case where there is no overlap between the X-ray pulses.
Figure 9:
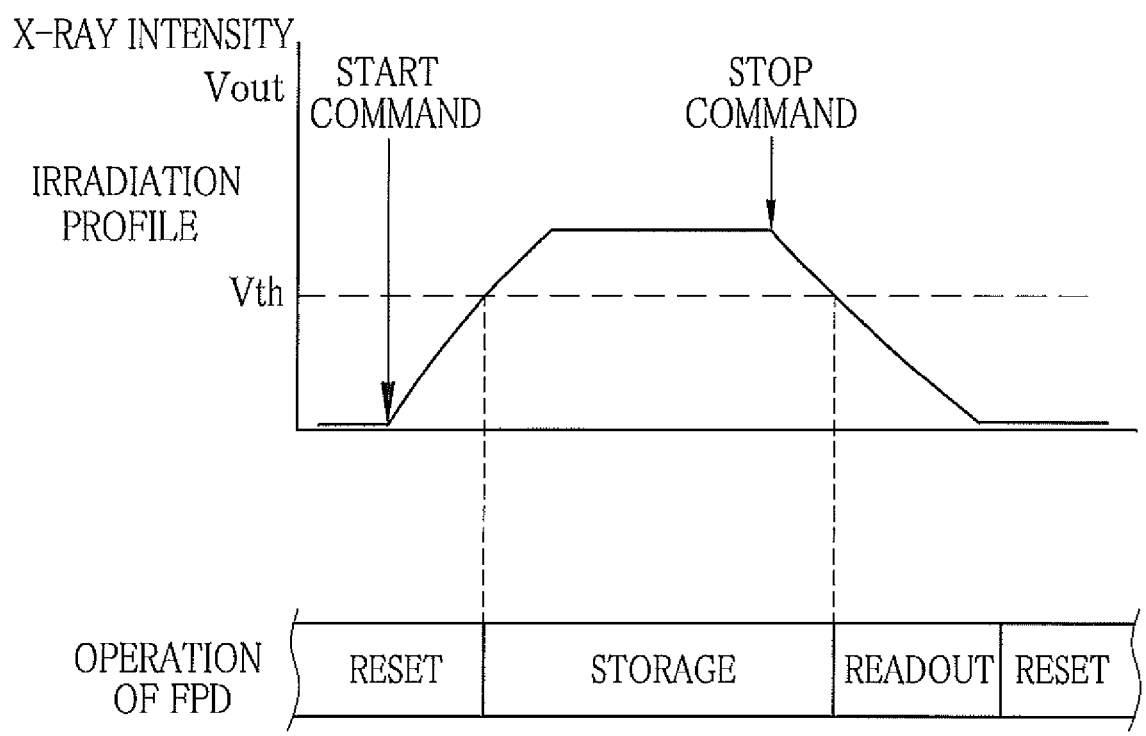
FIG. 9 is an explanatory view illustrating an irradiation profile of still image capture and the operations of the FPD.

In the pulse irradiation mode, the FPD 36 performs the fluoroscopy in steps shown in the flow chart in FIG. 7 and the timing chart in FIG. 8. When a command (imaging preparation command) for imaging preparation is inputted, the FPD 36 shifts from a stop state to a standby state. Thereby the reset operation is started (S101). Also, the measurement of the X-ray intensity is started (S102). The X-ray intensity is measured by monitoring an output voltage Vout of the short-circuited pixel 62.

When the irradiation start signal is inputted to the X-ray source 13 by pressing the irradiation start switch 15, the X-ray source 13 generates the X-ray pulses, in accordance with the input of the start command and the stop command, to start the pulsed X-ray irradiation in which the X-ray pulses are emitted to the subject H at regular time intervals as shown in FIG. 8. The controller 41 compares the output voltage Vout with the threshold voltage Vth to monitor a change in the X-ray intensity (S103). As shown in FIG. 8, the controller 41 detects that the X-ray irradiation is started when the X-ray intensity increases and the output voltage Vout exceeds the threshold voltage Vth (S104). Upon detecting the start of the X-ray irradiation, the controller 41 allows starting the storage operation (S105).

During the storage operation, the FPD 36 compares the output voltage Vout with the threshold voltage Vth to monitor a change in the X-ray intensity (S106). As shown in FIG. 8, when the X-ray intensity of the X-ray pulse starts decreasing and the output voltage Vout becomes less than or equal to the threshold voltage Vth, the FPD 36 detects that the irradiation is ended (S107). The FPD 36 ends the storage operation in synchronization with the detection of the end of the irradiation (S108). Upon ending the storage operation, the FPD 36 performs the readout operation. Upon ending the readout operation, the FPD 36 performs the reset operation until the start of the next irradiation is detected (S109). The read X-ray image is recorded in the memory 56. The FPD 36 repeats the steps S103 to S109 during the duration of the pulse irradiation from the X-ray source 13 (S110). Thereby the fluoroscopy of the object is performed. Two or more images, each captured per X-ray pulse, are sequentially transmitted from the memory 56 to the console 24, and displayed on the console 24.

The FPD 36 is set to the pulse irradiation mode in a case where a still image is captured. In this case, as shown in FIG. 9, the imaging operation ends without repeating it because the X-rays are emitted only once in capturing the still image (N in S110).

Figure 10:
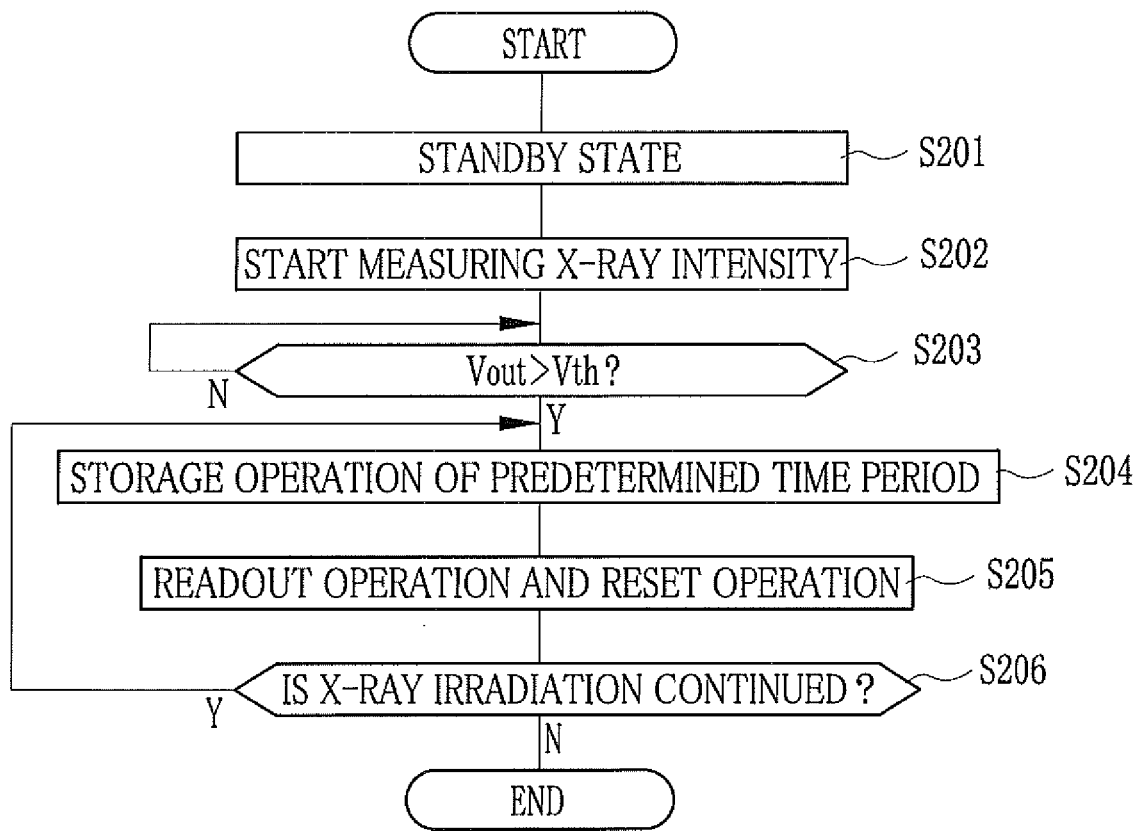
FIG. 10 is a flowchart illustrating steps for controlling the FPD in a successive irradiation mode.
Figure 11:
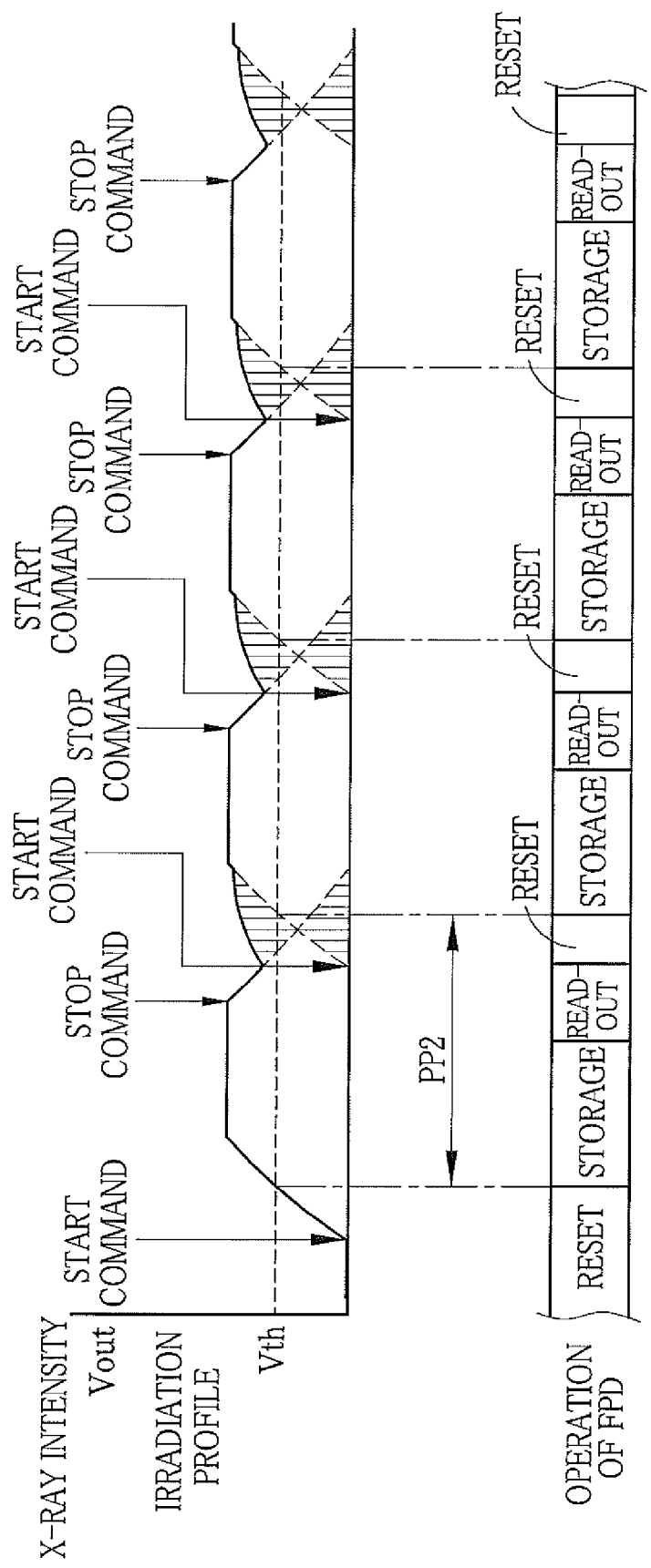
FIG. 11 is an explanatory view illustrating an irradiation profile and the operations of the FPD in a case where the X-ray pulses overlap each other.

In the successive irradiation mode, the FPD 36 performs the fluoroscopy in the steps shown by the flowchart in FIG. 10 and the timing chart in FIG. 11. The FPD 36 shifts from the stop state to the standby state when the imaging preparation command is inputted thereto. Thereby the FPD 36 starts the reset operation (S201). Also, the FPD 36 starts monitoring the output voltage Vout of the short-circuited pixel 62 to measure the X-ray intensity (S202).

When the irradiation start signal is inputted to the X-ray source 13 by pressing the irradiation start switch 15, the X-ray source 13 generates the X-ray pulse in accordance with the input of the start command and the stop command as shown in FIG. 11. The X-ray source 13 starts the pulse irradiation in which the X-ray pulses are emitted at regular time intervals to the subject H. The controller 41 compares the output voltage Vout with the threshold voltage Vth to monitor a change in the X-ray intensity (S203). As shown in FIG. 11, the controller 41 detects that the X-ray irradiation is started when the X-ray intensity increases and the output voltage Vout exceeds the threshold voltage Vth (Y in S203). The steps so far are similar to those in the pulse irradiation mode.

Figure 6:
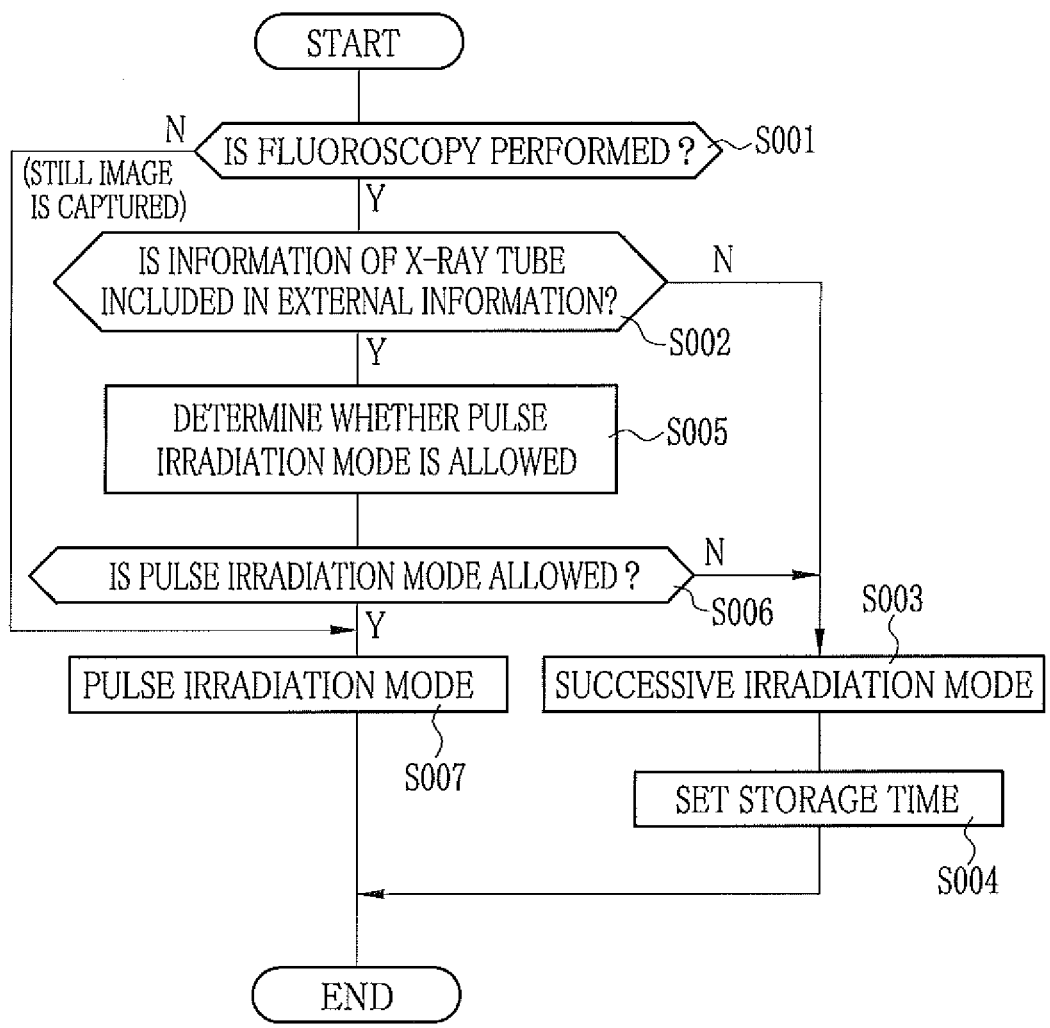
FIG. 6 is a flowchart illustrating a mode setting process.

In the successive irradiation mode, when the start of the irradiation is detected, the FPD 36 starts the storage operation of a predetermined time period which has been set in a mode setting process described in FIG. 6 (S204). After the predetermined time period, the FPD 36 ends the storage operation and performs the readout operation and then the reset operation (S205). When the reset operation ends, the FPD 36 repeats the storage operation, the readout operation, and the reset operation at predetermined time intervals. During the duration of the X-ray pulse irradiation from the X-ray source 13, the FPD 36 repeats the steps S204 and S205 (S206).

In the successive irradiation mode, the storage operation time refers to a time period calculated based on the pulse period PP obtained from the frame rate in the mode setting process (see FIG. 6). Hence, the fluoroscopy is performed at a frame rate synchronized with the pulse period PP even if the synchronous control is not allowed.

In this example, the storage operation is started in synchronization with the timing of the detection of the first X-ray pulse emitted. Then the storage operation is repeated in synchronization with the pulse period PP. Thereby the timing of the readout operation and the timing of the reset operation after the storage operation are synchronized with the valley between the two X-ray pulses in which the X-ray intensity decreases.

As described above, according to the X-ray image detection device 21 of the present invention, in a case where the fluoroscopy is performed using the pulse irradiation, an appropriate operation mode of the FPD 36 is determined based on the external information. In a case where the synchronous control is allowed, the FPD 36 operates in the pulse irradiation mode. In a case where the synchronous control is not allowed, the FPD 36 operates in the successive irradiation mode. Thus, the operation control is performed properly in accordance with the irradiation profile.

An X-ray image detection device capable of the synchronous control only, for example, a conventional device disclosed in the Japanese Patent Laid-Open Publication No. 2006-122667, may not be able to perform the fluoroscopy, depending on the irradiation profile of the X-ray source 13. In this case, it is necessary to employ an expensive X-ray tube, which has a fast response speed to detect the fall of the X-ray pulse, in order to use the X-ray image detection device of the Japanese Patent Laid-Open Publication No. 2006-122667. On the other hand, the X-ray image detection device 21 of the present invention determines whether the pulse irradiation mode is allowed based on the external information. In the case where the pulse irradiation mode is allowed, the synchronous control is performed in the pulse irradiation mode. In the case where the pulse irradiation mode is not allowed (in the case where the synchronous control is not allowed), the successive irradiation mode is set. There is no need to use the expensive X-ray tube. The fluoroscopy is performed with a commonly-used X-ray tube. Hence, there is no increase in cost incurred by replacement of the X-ray tube, for example. The X-ray image detection device 21 can be used flexibly and has excellent usability in a case where the X-ray image detection device 21 is used in combination with the conventional X-ray generating apparatus.

The operation mode is automatically set to the pulse irradiation mode or the successive irradiation mode in accordance with the external information. A complicated setting operation by an operator is unnecessary even if the X-ray image detection device 21 is used in combination with the X-ray generating apparatus 11 incapable of communication.

Whether the synchronous control is allowed or not depends on the overlapping state of the X-ray pulses in the irradiation profile. As described above, the overlapping state of the X-ray pulses is determined by various factors such as the type of the X-ray tube 13a, the tube current, the tube voltage, and the frame rate. For this reason, in the present invention, the determination table is produced in advance. The determination table is used for determining whether the overlap of the X-ray pulses exists based on the type of the X-ray tube 13a, the tube current, and the frame rate. Thereby whether the synchronous control is allowed is determined automatically. Thus, the effect of the present invention owing to the automatic determination with the use of the determination table has excellent usability.

Even if there is an overlap between the X-ray pulses, the synchronous control may be allowed if an overlapping portion of the X-ray pulses is small. In the pulse irradiation, whether the X-ray image detection device is capable of the synchronous control is determined by various factors such as performance of the X-ray tube, the pulse period (the frame rate of the fluoroscopy corresponding to the pulse period), and the imaging conditions (the tube current and the tube voltage) which determine the duration Ts of the wave tail of the X-ray pulse. In the present invention, the overlapping state of the X-ray pulses is checked based on the determination table, in which the above-described factors are taken into consideration, to determine whether the synchronous control is allowed. Thereby complicated operations by the operator such as checking the overlapping state through calculations are reduced significantly.

In a case where an irradiation profile has an extremely small amount of reduction in the X-ray intensity at the valley between the X-ray pulses, such irradiation profile may be regarded as equivalent to an irradiation profile of the X-rays continuously emitted at constant intensity from the X-ray source 13. In this case, in the successive irradiation mode, the FPD 36 may start the storage operation at arbitrary timing without the determination of the start timing of the storage operation.

In the above embodiment, the tube current is used to determine whether the pulse irradiation mode is allowed. Instead or in addition, the tube voltage may be used. In a case where both the tube current and the tube voltage are used for determining whether the pulse irradiation mode is allowed, accuracy of the determination is improved.

In the above embodiment, the determination table is produced for each type of the X-ray tube 13a. The types of the X-ray tubes 13a are categorized by the structures of the electrodes, such as the diode, the triode, and the tetrode, by way of example. Instead or in addition, the types of the X-ray tubes 13a may be categorized by materials of the targets (anodes). The target (anode) is a component of the X-ray tube 13a.

Tungsten (W), molybdenum (Mo), or the like may be used as the material of the target of the X-ray tube 13a. Values of the threshold voltage Vth shown in FIGS. 8 and 11 may be changed depending on the material of the target. For example, the threshold voltage Vth is set to approximately 15 kV for tungsten. The threshold voltage Vth is set to approximately 5 kV for molybdenum. In a case where the threshold voltage Vth varies with the material of the target, the rise and the fall of the X-ray pulse may or may not be detected even if the irradiation profile (the overlap of the two X-ray pulses) does not change. The result of determining whether the pulse irradiation mode is allowed also varies accordingly. For example, the rise and the fall of the X-ray pulse can be detected even in the irradiation profile shown in FIG. 11, if the threshold voltage Vth is greater than the minimum X-ray intensity at the valley between the two X-ray pulses.

Thus the threshold voltage Vth affects the result of determining whether the pulse irradiation mode is allowed or not. In a case where the threshold voltage Vth and the material of the target of the X-ray tube 13a are in one-to-one correspondence with each other, two or more determination tables are produced for each material of the target of the X-ray tube 13a. The material of the target is a factor which changes the threshold voltage Vth. One of the determination tables suitable for the material of the target of the X-ray tube 13a is chosen to be used. In some cases, the irradiation profile may change depending on the material of the target of the X-ray tube 13a. Even if the threshold voltage Vth does not change regardless of the material of the target, a change in the irradiation profile due to the material of the target may change the overlapping state of the two X-ray pulses and affect the result of determining whether the pulse irradiation mode is allowed. Thus, it is preferable to use the information related to the type of the X-ray tube 13a categorized by the material of the target because it affects the result of determining whether the pulse irradiation mode is allowed.

Note that the result of determining whether the pulse irradiation mode is allowed or not is affected by a change in the threshold voltage Vth even if the same X-ray tube 13a is used (the type of the X-ray tube 13a is not changed). Hence, instead of the type of the X-ray tube 13a, the threshold voltage Vth may be used as the external information for determining whether the pulse irradiation mode is allowed or not. In this case, two or more determination tables are produced for each threshold voltage Vth and the suitable one is used, for example.

In the above embodiment, the type of the X-ray tube 13a, which is a component of the X-ray generating apparatus 11, is described as the information related to the X-ray generating apparatus 11, by way of example. Instead, in a case where the type of the X-ray tube 13a is identified by the name of the manufacturer, the model type, or the specification information of the X-ray generating apparatus 11, the X-ray source 13, or the X-ray source control device 14, such information for identifying the type of the X-ray tube 13a may be used as the information related to the X-ray generating apparatus 11. For example, in a case where the irradiation profile of the X-ray tube 13a is determined by the combination of the X-ray tube 13a and the X-ray source control device 14, both of information related to the type of the X-ray tube 13a and information related to the type of the X-ray source control device 14 may be used as the information related to the X-ray generating apparatus 11. In this case, the determination table is produced per combination of the type of the X-ray tube 13a and the type of the X-ray source control device 14.

As for the external information for determining whether the pulse irradiation mode is allowed or not, physique information including at least one of a site to be captured, the thickness of the body, the age (an adult or a child), and the gender of the subject H may be used in addition to the information related to the X-ray generating apparatus 11 and the imaging conditions. The X-ray passed through the subject H and attenuated by the subject H are incident on the FPD 36. An attenuation value of the X-rays caused by the subject H varies depending on the site to be captured and the physique of the subject H. Hence, the irradiation profile detected by the FPD 36 varies depending on the site to be captured and the physique of the subject H even if the imaging conditions such as the tube voltage V, the tube current I, and the frame rate of the fluoroscopy do not change. As described above, a change in the irradiation profile may affect the result of determining whether the pulse irradiation mode is allowed or not. For this reason, two or more determination tables may be produced for each site to be captured or each physique, for example. The determination table suitable for the site to be captured is chosen to be used.

Thus, various factors affect the determination of whether the pulse irradiation mode is allowed or not. Hence, it is preferable to produce two or more determination tables in consideration of two or more types of the external information such as the type of the X-ray tube 13a described above, the imaging conditions, the threshold voltage Vth, the site (object) of the subject H to be captured, and the physique. The suitable determination table is chosen to be used.

Note that a mathematical expression using the external information as a parameter may be created in advance, instead of the determination table. The determination section may output the result of the determination calculated using the mathematical expression.

In the above embodiment, the determination section 64 is disposed in the X-ray image detection device 21. Alternatively, the determination section 64 may be provided in one of the imaging control device 23 and the console 24 which are peripheral devices of the X-ray image detection device 21. In the above embodiment, the X-ray image detection device 21 and the imaging control device 23 are provided separately. In a case where the X-ray image detection device 21 integrates with the imaging control device 23, for example, in a case where the function of the imaging control device 23 is incorporated in the controller 41 of the X-ray image detection device 21, the determination section 64 may be provided in the console 24 that is one of the peripheral devices.

The determination section 64 and the determination table 65 may not necessarily be provided in the same device. For example, the determination section 64 may be provided in one of the X-ray image detection device 21, the imaging control device 23, and the console 24. The determination table 65 may be provided in the device other than the device provided with the determination section 64.

The determination table 65 may not be provided in the X-ray image detection device 21, the imaging control device 23, or the console 24. For example, the determination table 65 may be provided in a data storage device such as a server connected to the imaging control device 23 or the console 24 through a communication network. In this case, the determination section 64 provided in one of the X-ray image detection device 21, the imaging control device 23, and the console 24 accesses the data storage device through the communication network, and obtains the information from the determination table 65.

In the above embodiment, the determination table 65 is used to determine whether the pulse irradiation mode is allowed or not. Instead of using the determination table 65, for example, the determination section 64 may calculate the overlapping state of the X-ray pulses based on the external information, to determine whether the pulse irradiation mode is allowed or not. The overlapping state of the X-ray pulses is obtained from the duration of the wave tail of the X-ray pulse and the X-ray pulse period PP. The duration of the wave tail of the X-ray pulse is calculated using the above-described time constant $\tau$. The X-ray pulse period PP is obtained from the frame rate. The calculation of the overlapping state saves the operator from having to create the determination table (s) in advance. There is no need for the operator to perform a complicated operation because the determination section 64 performs the calculations.

Note that, in the above example, in the pulse irradiation mode, the storage operation is started when the rise of the X-ray pulse is detected, and the readout operation is started when the fall of the X-ray pulse is detected. Alternatively, for example, the storage operation may be started at a predetermined time period after the detection of the rise. The readout operation may be started at a predetermined time period after the detection of the fall. Namely, the detected timing of the rise does not necessarily coincide with the start timing of the storage operation as long as the start timing of the storage operation is determined based on the detected timing of the rise. The detected timing of the fall does not necessarily coincide with the start timing of the readout operation as long as the start timing of the readout operation is determined based on the detected timing of the fall.

The radiation detector for measuring the X-ray intensity is not limited to the short-circuited pixel and may take various forms. For example, a bias voltage is applied to the photodiode constituting the pixel. A bias current passing through a bias line varies depending on an amount of a signal charge generated in the photodiode. The X-ray intensity may be measured by detecting the bias current. A small amount of leakage current passes through a signal line in accordance with the amount of the signal charge generated in the photodiode even if the TFT of the pixel is in an OFF state. The X-ray intensity may be measured by detecting the leakage current.

In a method for detecting a bias current or a leakage current, the radiation detector is composed of wiring disposed in the FPD 36 and an ammeter. The bias current or the leakage current passes through the wiring. The ammeter detects the current passing through the wiring. The method for detecting the bias current or the leakage current adds a function of the radiation detector to the FPD 36 without a significant change in the structure of the image capture field of the FPD 36. In a case where the method for detecting the leakage current is employed, an image reading circuit of the FPD 36 may be used as a current detector. The method for detecting the bias current or the leakage current is advantageous in preventing pixel defects (point defects or line defects) in the image because the storage of the signal charges, which represents an image, is maintained even if the radiation is detected during the irradiation.

Instead of providing the short-circuited pixel, a part of the pixels 37 in the FPD 36 may serve also as detection elements constituting the radiation detector. For example, for each pixel also serving as the detection element, a TFT for detecting the radiation and wiring dedicated to the radiation detection are provided in addition to the TFT for reading an image. When an image is read out, the TFT for reading the image is turned on and the charge is read out through the signal line. In a case where the pixel is used as the detection element, a gate of the TFT for detecting the radiation is turned on and the charge is read out through the wiring dedicated to the radiation detection. Thus, the two TFTs are selectively used. Instead, the leakage current, which leaks from the TFT to the dedicated wiring when the TFT is in the off state, may be read out. In the case where a part of the pixels 37 also serves as the detection elements, the photodiode of the pixel 37 may be divided into two, for example, a photodiode for detecting an image and a photodiode for detecting the radiation. A TFT is provided in each divided photodiode. The TFTs are selectively used.

In a case where exclusive detection elements constituting the radiation detector are provided in addition to the pixels 37, the detection elements may be disposed between the pixels 37. The detection elements may be disposed outside of the image capture field. A well-known radiation detector such as an ion chamber may be used as the radiation detector.

The TFT-type FPD with the TFT matrix substrate made from a glass substrate is used by way of example. Instead, a CMOS image sensor or a CCD image sensor using a semiconductor substrate may be used. The CMOS image sensor has the following advantages. The CMOS image sensor allows the so-called nondestructive reading in which the signal charge stored in each pixel is read out as a voltage signal through an amplifier provided to each pixel, with no flow through the signal line for reading. Thereby, the X-ray intensity is measured by choosing a desired pixel in the image capture field and reading out the signal charge from the chosen pixel, even during the storage operation. Thus, in the case where the CMOS image sensor is used, one or some of the pixels serve also as the radiation detector for measuring the X-ray intensity. There is no need to use the radiation detector, used exclusively for the measurement of the X-ray intensity, such as the above-described short-circuited pixel.

The X-ray imaging apparatus according to the present invention is not limited to those described in the above embodiment. The X-ray imaging apparatus may take various forms as long as it is within the scope of the present invention.

The X-ray imaging apparatus is used in an X-ray imaging system installed in an imaging room of a hospital. The X-ray imaging apparatus may be installed on movable medical equipment which allows X-ray imaging at a patient's bed. The X-ray imaging apparatus may be applied to a portable system which is carried to a location of an accident or disaster where emergency medical care is necessary or a home of a home-care patient.

In the above example, the X-ray image detection device and the imaging control device are provided separately. The X-ray image detection device and the imaging control device may be integrated by incorporating a function of the imaging control device in a controller of the X-ray image detection device.

In the above embodiment, an electronic cassette is described by way of example. The electronic cassette is a portable X-ray detection device. The present invention is also applicable to a stationary type X-ray image detection device.

The present invention is not limited to the imaging system using the X-rays. The present invention is also applicable to an imaging system using another type of the radiation such as gamma rays.

Various changes and modifications are possible in the present invention and may be understood to be within the present invention.

What is claimed is:

1. An X-ray radiation imaging apparatus used in combination with an X-ray radiation generating apparatus, for performing fluoroscopy, the X-ray radiation generating apparatus successively generating pulses of X-ray radiation to perform pulse irradiation, the X-ray radiation imaging apparatus comprising:
   an image detector for detecting an X-ray radiation image of an object, the image detector having an image capture field in which pixels are arranged in a matrix, each pixel storing a signal charge in accordance with a dose of the X-ray radiation;
   an X-ray radiation detector for detecting the X-ray radiation and outputting a detection signal in accordance with the dose;
   a controller for allowing the image detector to operate in one of a pulse irradiation mode and a successive irradiation mode, the controller detecting a rise and a fall of the pulse of the X-ray radiation based on the detection signal outputted from the X-ray radiation detector and determining start timing of a storage operation based on timing of detecting the rise and determining start timing of a readout operation based on timing of detecting the fall in the pulse irradiation mode, the signal charge being stored in the storage operation, the stored signal charge being read out in the readout operation, the storage operation and the readout operation being repeated alternately at predetermined time intervals without detection of the rise and the fall of the pulse of the X-ray radiation in the successive irradiation mode;
   a determination section for obtaining external information, which includes information related to the X-ray radiation generating apparatus and imaging conditions, and determining whether the image detector is allowed to be set to the pulse irradiation mode based on the obtained external information; and
   a mode setting section for setting the image detector to one of the pulse irradiation mode and the successive irradiation mode based on a result of determination of the determination section, the mode setting section setting the image detector to the pulse irradiation mode in a case where the image detector is allowed to be set to the pulse irradiation mode, the mode setting section setting the image detector to the successive irradiation mode in a case where the image detector is not allowed to be set to the pulse irradiation mode.

2. The X-ray radiation imaging apparatus of claim 1, wherein the external information is information for determining an overlapping state of a rising edge and a falling edge of two successive pulses of the X-ray radiation during the pulse irradiation.

3. The X-ray radiation imaging apparatus of claim 2, wherein the information related to the X-ray radiation generating apparatus is a type of an X-ray radiation tube constituting the X-ray radiation generating apparatus, and the imaging condition is at least one of a frame rate of the fluoroscopy, a tube current supplied to the X-ray radiation tube, and a tube voltage supplied to the X-ray radiation tube.

4. The X-ray radiation imaging apparatus of claim 3, further comprising a determination table against which the determination section checks the external information to determine whether the pulse irradiation mode is allowed.

5. The X-ray radiation imaging apparatus of claim 4, wherein the determination table stores information of whether the pulse irradiation mode is allowed, per combination of three types of information, and the three types of information include the type of the X-ray radiation tube, at least one of the tube current and the tube voltage, and the frame rate.

6. The X-ray radiation imaging apparatus of claim 4, wherein the determination section sets the image detector to the successive irradiation mode in a case where the determination section cannot obtain the external information necessary for determining whether the pulse irradiation mode is allowed.

7. The X-ray radiation imaging apparatus of claim 4, further comprising an X-ray radiation image detection device having the image detector, the controller, and a housing for accommodating the image detector and the controller.

8. The X-ray radiation imaging apparatus of claim 7, wherein the X-ray radiation image detection device comprises the determination section.

9. The X-ray radiation imaging apparatus of claim 8, wherein the X-ray radiation image detection device has the determination table.

10. The X-ray radiation imaging apparatus of claim 7, wherein the X-ray radiation image detection device has the X-ray radiation detector.

11. The X-ray radiation imaging apparatus of claim 7, further comprising a peripheral device separate from the X-ray radiation image detection device, and the determination section is provided in the peripheral device.

12. The X-ray radiation imaging apparatus of claim 2, wherein the determination section calculates the overlapping state based on the external information, to determine whether the pulse irradiation mode is allowed.

13. The X-ray radiation imaging apparatus of claim 1, wherein the controller allows starting the storage operation at the timing of detecting the rise of the pulse of the X-ray radiation in the pulse irradiation mode.

14. The X-ray radiation imaging apparatus of claim 1, wherein the controller ends the storage operation and allows starting the readout operation at the timing of detecting the fall of the pulse of the X-ray radiation in the pulse irradiation mode.

15. The X-ray radiation imaging apparatus of claim 1, wherein the X-ray radiation imaging apparatus is capable of performing still image capture in addition to the fluoroscopy.

16. The X-ray radiation imaging apparatus of claim 15, wherein the controller detects the rise and the fall of the pulse of the X-ray radiation based on the detection signal of the X-ray radiation detector and synchronizes the storage operation with the rise and synchronizes the readout operation with the fall in the still image capture, in a manner similar to the pulse irradiation mode.

17. The X-ray radiation imaging apparatus of claim 1, wherein the image capture field includes at least one short-circuited pixel in addition to pixels, and the at least one short-circuited pixel is constantly short-circuited with a signal line for reading out the signal charge from the pixel, and
wherein the X-ray radiation detector is the at least one short-circuited pixel which constantly outputs a signal charge corresponding to the dose to the signal line.

18. An X-ray radiation image detection device used in combination with an X-ray radiation generating apparatus, for performing fluoroscopy, the X-ray radiation generating apparatus successively generating pulses of X-ray radiation to perform pulse irradiation, the X-ray radiation image detection device comprising:
  an image detector for detecting an X-ray radiation image of an object, the image detector having an image capture field in which pixels are arranged in a matrix, each pixel storing a signal charge in accordance with a dose of the X-ray radiation;
  an X-ray radiation detector for detecting the X-ray radiation and outputting a detection signal in accordance with the dose;
  a controller for allowing the image detector to operate in one of a pulse irradiation mode and a successive irradiation mode, the controller detecting a rise and a fall of the pulse of the X-ray radiation based on the detection signal outputted from the X-ray radiation detector and determining start timing of a storage operation based on timing of detecting the rise and determining start timing of a readout operation based on timing of detecting the fall in the pulse irradiation mode, the signal charge being stored in the storage operation, the stored signal charge being read out in the readout operation, the storage operation and the readout operation being repeated alternately at predetermined time intervals without detection of the rise and the fall of the pulse of the X-ray radiation in the successive irradiation mode;
  a determination section for obtaining external information, which includes information related to the X-ray radiation generating apparatus and imaging conditions, and determining whether the image detector is allowed to be set to the pulse irradiation mode based on the obtained external information; and
  a mode setting section for setting the image detector to one of the pulse irradiation mode and the successive irradiation mode based on a result of determination of the determination section, the mode setting section setting the image detector to the pulse irradiation mode in a case where the image detector is allowed to be set to the pulse irradiation mode, the mode setting section setting the image detector to the successive irradiation mode in a case where the image detector is not allowed to be set to the pulse irradiation mode.

19. A method for controlling an X-ray radiation imaging apparatus used in combination with an X-ray radiation generating apparatus, for performing fluoroscopy, the X-ray radiation generating apparatus successively generating pulses of X-ray radiation to perform pulse irradiation, the X-ray radiation imaging apparatus comprising an X-ray radiation detector and an image detector for detecting an X-ray radiation image of an object, the image detector having pixels arranged in a matrix, each pixel storing a signal charge in accordance with a dose of the X-ray radiation, the X-ray radiation detector detecting the X-ray radiation and outputting a detection signal in accordance with the dose; the method comprising the steps of:
  obtaining external information that includes information related to the X-ray radiation generating apparatus and imaging conditions;
  determining whether the image detector is allowed to be set to a pulse irradiation mode based on the external information, a rise and a fall of the pulse of the X-ray radiation being detected based on the detection signal outputted from the X-ray radiation detector and start timing of a storage operation for storing the signal charge being determined based on timing of detecting the rise and start timing of a readout operation for reading out the signal charge being determined based on timing of detecting the fall in the pulse irradiation mode;

setting the image detector to the pulse irradiation mode in a case where the image detector is allowed to be set to the pulse irradiation mode, and setting the image detector to a successive irradiation mode in a case where the image detector is not allowed to be set to the pulse irradiation mode, the storage operation and the readout operation being repeated alternately at predetermined time intervals without detection of the rise and the fall of the pulse of the X-ray radiation in the successive irradiation mode; and controlling the image detector in one of the pulse irradiation mode and the successive irradiation mode to which the image detector is set.

* * * * *